United States Patent
Douglas et al.

(10) Patent No.: US 6,843,135 B2
(45) Date of Patent: Jan. 18, 2005

(54) METHOD AND APPARATUS FOR REMOTELY MONITORING CORROSION USING CORROSION COUPONS

(75) Inventors: Dennis G. Douglas, Bend, OR (US); Joseph W. Maresca, Jr., Sunnyvale, CA (US); Christopher M. Smith, Richland, WA (US); Phillip C. Ohl, Kennewick, WA (US)

(73) Assignee: Vista Engineering Technologies LLC, Kennewick, WA (US)

( * ) Notice: Subject to any disclaimer, the term of this patent is extended or adjusted under 35 U.S.C. 154(b) by 40 days.

(21) Appl. No.: 10/611,361

(22) Filed: Jun. 30, 2003

(65) Prior Publication Data

US 2004/0055391 A1 Mar. 25, 2004

Related U.S. Application Data

(60) Provisional application No. 60/392,984, filed on Jun. 28, 2002.

(51) Int. Cl.[7] .............................................. G01N 19/08
(52) U.S. Cl. ......................................... 73/799; 73/810
(58) Field of Search ................................... 73/799, 810

(56) References Cited

U.S. PATENT DOCUMENTS

| | | | |
|---|---|---|---|
| 3,609,549 A | * 9/1971 | Hausler et al. ............. | 324/700 |
| 3,936,737 A | * 2/1976 | Jefferies, Sr. ............... | 324/700 |
| 4,120,313 A | 10/1978 | Lewis ......................... | 137/268 |
| 4,181,882 A | * 1/1980 | Isaacs et al. .............. | 205/775.5 |
| 4,238,298 A | * 12/1980 | Tsuru et al. .............. | 205/775.5 |
| 4,267,148 A | 5/1981 | Dickson et al. ............... | 422/53 |
| 5,139,627 A | * 8/1992 | Eden et al. .............. | 205/775.5 |
| 5,284,061 A | 2/1994 | Seeley et al. .................. | 73/746 |
| 5,297,940 A | * 3/1994 | Buse ........................... | 417/63 |
| 5,446,369 A | * 8/1995 | Byrne et al. ............... | 324/71.2 |
| 5,728,943 A | * 3/1998 | Colter et al. ................... | 73/799 |
| 6,067,855 A | 5/2000 | Brown et al. ................. | 73/308 |
| 6,182,514 B1 | 2/2001 | Hodges ....................... | 73/722 |
| 6,499,353 B1 | 12/2002 | Douglas et al. ............... | 73/722 |
| 6,628,111 B2 | * 9/2003 | Shapiro et al. ............ | 324/71.2 |

* cited by examiner

Primary Examiner—Max Noori
(74) Attorney, Agent, or Firm—David Jaffer; Pillsbury Winthrop LLP

(57) ABSTRACT

A method and an apparatus for remotely and automatically monitoring for corrosion of a tank, pipe, or container with a gas or liquid environment using corrosion coupons that do not have to be removed from the environment for inspection and evaluation. The coupons are designed to fail when a specified level of corrosion occurs. A permanent magnet located on a coupon sensing system inside the corrosive environment is used to transmit the failure of the coupons outside the corrosion environment and across a wall or other boundary surface without requiring a power supply.

29 Claims, 19 Drawing Sheets

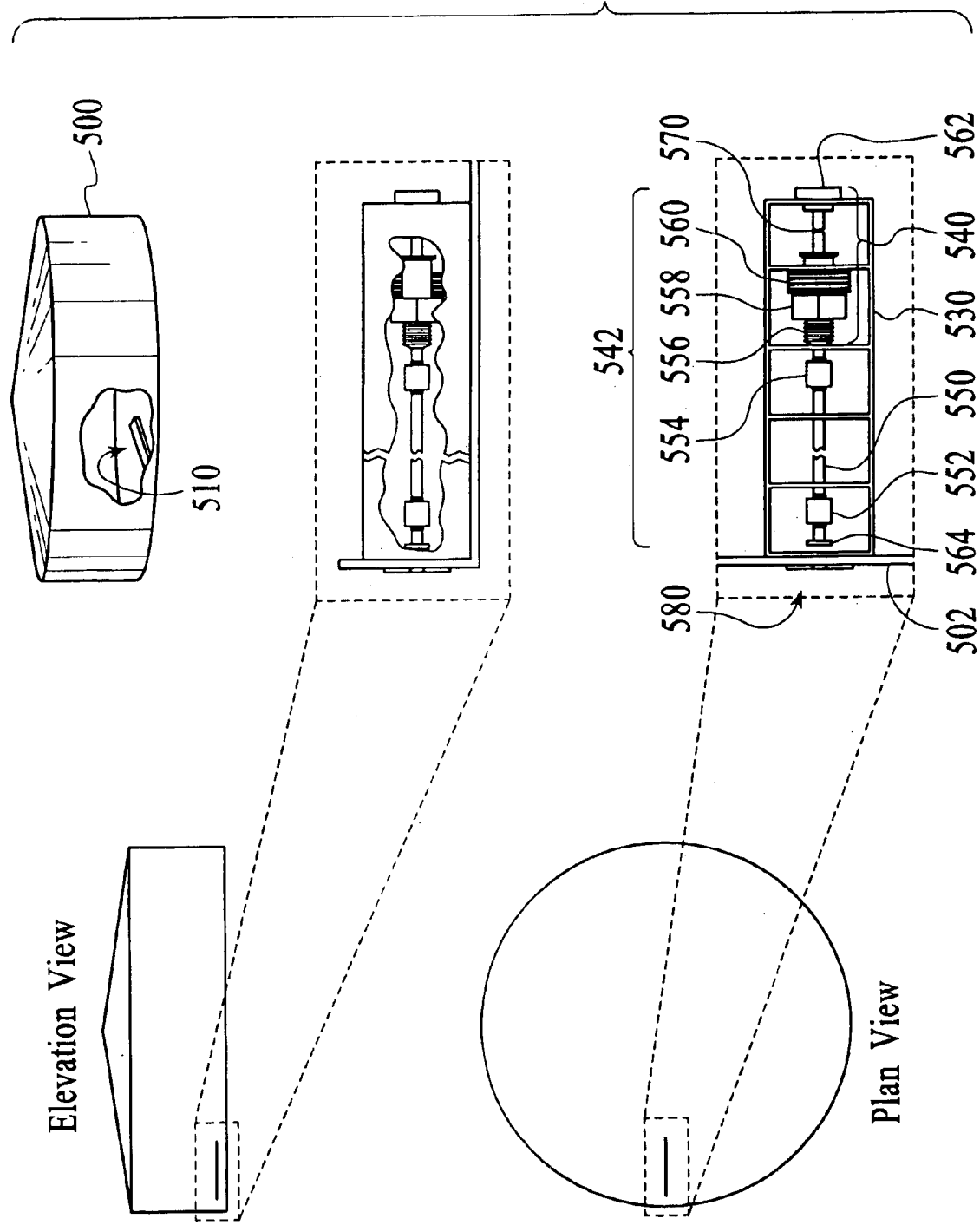

METHOD AND APPARATUS FOR REMOTELY MONITORING CORROSION USING CORROSION COUPONS

This application claims the benefit of provisional application No. 60/392,984, filed Jun. 28, 2002.

BACKGROUND OF THE INVENTION

1. Field of the Invention

A method for detecting the presence of corrosion of a structure (e.g., wall, container, vessel, tank, or pipe) using a magnetically coupled sensing system that remotely monitors the health of one or more corrosion coupons. It is best used when physical access to the coupon is difficult, costly, or impossible.

2. Description of the Prior Art

Corrosion will reduce the useful life of a structure. Corrosion may result in the thinning of the structure, pitting of the structure, or cracking of the structure. The type of corrosion that may occur and the type of corrosion monitoring systems needed to assess the degree of corrosion will depend on the service environment of the structure and the condition and operational use of the structure. There are three basic approaches to corrosion monitoring. The first is to make a "direct" measurement of the physical properties of the structure itself. The second is to use a "surrogate" material positioned in the service area, which is identical to the material in the structure, and infer the corrosion of the structure from the surrogate material. The third is to monitor the "chemistry" of the solution or gas upstream, downstream or within the service environment and then infer the effects of corrosion on the structure from an empirical or theoretical relationship that relates the measured quantity to the corrosion-induced damage.

The objective of all three corrosion-monitoring methods is to predict the remaining useful life of the structure of interest from an estimate of the corrosion measured or inferred with the monitoring method. In the case of monitoring the structure directly, a simple extrapolation can be made once several time-sequenced measurements have been made. In the case of either monitoring corrosive chemistry or monitoring surrogates, an inference must be made that correlates the corrosion measurement taken to the actual impacts on the structure.

Direct monitoring is a preferred method, but due to access, safety, or cost implications, this approach is not always viable. Direct monitoring may involve visual or photographic inspection of the structure, or physical measurements of the dimensions of the structure (e.g., (1) wall thickness; (2) pit depth, diameter or pit density; or (3) crack depth, width, length or density). For many structures in which one side of the structure is accessible, the use of non-destructive examination equipment such as ultrasonic or eddy current techniques can be used to provide general wall thickness data or cross-sectional imaging. The main problem with direct monitoring is the access to the structure is needed and in many instances, access is not possible. Such measurements cannot be practically be made, for example, in radioactive storage containers, or on the walls of underground or the floor of aboveground storage tanks and piping containing petroleum or other hazardous substances and hazardous waste. For these types of applications, surrogate monitoring and chemistry monitoring systems are normally employed.

There are commercially available corrosion monitoring techniques that involve direct monitoring of a surrogate. The surrogate material is typically made of the same material as the structure of interest. The most common surrogate monitoring approach is the direct placement of corrosion coupons in the environment of interest. Corrosion coupons are the lowest-tech method of corrosion monitoring via surrogates. A corrosion coupon is a piece of material similar (identical) to the material of interest. The corrosion coupon(s) are placed in similar service conditions and then removed from the service area and evaluated at a later date. These coupon inspections are done periodically and are not linked to a specific level of corrosion. The coupons may be analyzed using destructive metallography. They may be inspected for appearance and/or weighed and compared to the pre-service weight do determine material loss. The use of corrosion coupons, while viewed as a very good method of assessing corrosion, is typically expensive and inconvenient to use. In some instances, the structure needs to be taken out of service to remove the coupons from the service area, which is expensive and may have health and safety implications. As presently used, corrosion coupons do not give any early warning of impending failure until they are retrieved and examined.

Electrical Resistance (ER) and Linear Polarization Resistance (LPR) probes both rely on electrical current being passed through a surrogate material and measuring changes in the resistance of the electrical circuit as the surrogate material degrades. Essentially, current is passed through a known cross-section; as metal disappears, resistance increases. Both ER and LPR probes are effective means for measuring uniform corrosion; however, correlating the change in resistance of an ER or LPR probe to the physical changes to the structure caused by corrosion can be imprecise and not yield good answers for many applications.

Developed for, and applied at, the U.S. Department of Energy's (DOE's) Hanford tank farms, electrochemical noise corrosion probes measure corrosion current and potential (voltage) between three surrogate electrodes. The relationship between corrosion current and corrosion potential on each electrode is indicative of the type and magnitude of corrosion on the electrodes, which can then infer the type and magnitude of corrosion on the structure. While electrochemical noise is a viable technology for early warning of stress corrosion cracking and pitting, its ability to quantify corrosion in a new application requires confirmatory laboratory corrosion studies in order to reliably correlate corrosion probe data with degradation of the structure.

A Thin-Wall Membrane Corrosion Probe is a one-shot vacuum chamber with a thin-wall membrane and a sensor. When the thin wall is breached by a through-wall pit, a signal is generated. This device operates somewhat like a balloon; when the balloon is "popped", the pressure change is used to indicate the breach. This device is an excellent pitting corrosion detector.

The present invention describes a method and apparatus for remotely and automatically determining the amount and rate of corrosion of a structure or the material in the structure in a difficult to access environment without the need to handle or remove the corrosion coupon from the environment. The patent literature does not describe any such invention using corrosion coupons. U.S. Pat. No. 4,120,313 describe holding and/or handling systems for corrosion coupons. There are however, numerous inventions in the patent literature that describe electrical noise, electrical resistance and linear polarization methods and apparatuses. For example, U.S. Pat. Nos. 3,609,549; 3,936,737; 4,181,882; 4,238,298; 5,139,627; 5,446,369 describe such inventions.

In U.S. Pat. No. 6,499,353, Douglas, et. al., describes a magnetically coupled pressure gauge that measures the pressure or temperature inside a seal container and generates magnetic signal outside the container that yields a continuous measurement of pressure or temperature. In U.S. Pat. No. 5,284,061, Seeley, et. al., describes an apparatus for measuring pressure change of a specified amount in a sealed container that is mainly intended to detect a gas leak due to a loss of pressure. In U.S. Pat. No. 6,182,514, Hodges describes a pressure monitoring system for seal containers using bellows and magnet to monitor pressure. In U.S. Pat. No. 6,067,855, Brown, et. al., describes an apparatus for measuring liquid level in a container, which communicates the level changes of a float riding on the liquid surface to the outside of the container using magnetic sensing strip. None of these systems monitor corrosion and none of these systems use corrosion coupons.

The present invention was initially conceived to address a potential corrosion problem in a sealed stainless steel container holding radioactive material in a specialized container system known as a 3013 canister. However, the invention has extensive application to corrosion monitoring in general. It can be used to monitor corrosion in storage tanks and pipelines containing liquids and gases that may be corrosive to the walls of the tank or pipe. It has the potential for use in many less obvious application like furnaces and other structures where access is difficult.

API 653 requires the floor of an aboveground storage tank containing petroleum products be periodically inspected. The time between inspections can be increased and the inspections improved if the rate of corrosion of the floor or inside walls of the tank can be measured. The same is true for pipelines.

The present invention automates the use of corrosion coupons and mitigates the common and important disadvantages this approach. The coupon does not need to be removed from the service area for assessment, and periodic assessments are not required. Also, the present invention does not disturb the service environment, which occurs when coupons are removed. More importantly, the present invention indicates when a certain specified level of corrosion occurs. A time sequence of measurements can be made using multiple coupons. Coupons with different physical characteristics and/or loadings can be used to determine different types and different levels of corrosion. For example, a thin coupon can be used to indicate that corrosion is occurring, but at a level of negligible impact to the structure. A thicker coupon can be used to give an early warning of an important level of corrosion and may indicate that a more thorough inspection of the structure is required. Finally, an even thicker coupon may indicate that the structure needs replacement or upgrading.

In view of the prior art described above, it is apparent that there is a need and a wide range of applications for a method and apparatus that can remotely and automatically measure corrosion using coupons without requiring the removal of the coupons from the service environment.

SUMMARY OF THE INVENTION

It is therefore an object of the present invention to provide a method and an apparatus for measuring corrosion of a structure using one or more corrosion coupons without removing, handling, observing or assessing, qualitatively or quantitatively, the condition of the coupon or coupons.

It is another object of the present invention to provide a method and an apparatus for measuring corrosion using an automatic, remote monitoring, corrosion coupon system.

It is another object of the present invention to provide a method and an apparatus for measuring corrosion inside a tank, a pipe, or another type of container system storing, transferring, or processing liquids, gases, mixed phase solutions, or slurries (e.g. water, petroleum, radioactive substances) that do not require penetrating the walls of the containment system.

It is another object of the present invention to provide a method and an apparatus for measuring corrosion inside a sealed container that does not require penetrating the sealed container.

It is a still further object of the present invention to provide a method and an apparatus for measuring the failure of a corrosion coupon inside a containment system, especially those that are completely sealed, that does not require internal electrical power.

It is another object of the present invention to provide a method and an apparatus for measuring the failure of a corrosion coupon inside a containment system using permanent magnets for transmitting the corrosion data and not requiring internal electrical power.

Briefly, the present invention includes a method and an apparatus for remotely and automatically measuring corrosion in a difficult to access area or containment system, especially sealed containers storing or transporting radioactive materials, or storage tanks or piping storing or transferring water, petroleum products, or other hazardous substances/chemicals. It consists of a corrosion coupon system that is positioned inside and used to monitor for corrosion in a containment system in which access to or penetration of the walls is not desirable. The corrosion coupon system may contain a multiplicity of coupons and transmits a detectable magnetic signal as each coupon fails that is sensed outside the containment system. Each corrosion coupon inside the containment system will fail when a specified level of corrosion occurs. The magnetic signal is produced from a magnet that moves in response to the coupon failure. The coupon failure will allow the rotation or translation of a spring-loaded element. The magnetic signal produced by a change in position of the magnet, is measured/detected by a magnetic sensing system located on the outside of the containment system. The measured magnetic signal is then displayed using either a mechanical or electrical readout system.

The method and apparatus are comprised of (1) corrosion coupon transmitter, which is placed in the service environment to be monitored and (2) a receiver, which is usually located outside the service area, although this is not necessary and for some applications, it cannot be. The transmitter is comprised of (a) one or more corrosion coupons that are identical to the material in the structure that might corrode; (b) a rigid mounting system that holds and positions the corrosion coupons in the potentially corrosive environment; (c) a spring or coil in compression or tension that will change its position if the tension or compression is removed because of a coupon failure; and (d) a magnet that can be attached to the spring or coil so that the magnet or the magnetic field of the magnet changes if the spring or coil changes position because of a coupon failure. Alternatively, the magnet can be attached to another element that will change its position and the position of the magnet positioned on the element when a coupon fails. The movement of the magnetic may involve a rotation, translation or combination.

The receiver apparatus is comprised of a magnetic sensing unit that measures the change in the magnet field if the corrosion coupon fails. The magnetic sensing unit can be a mechanical system such as a compass whose needle will give a different reading when the magnet in the coupon transmitter apparatus changes position. The magnetic sensing unit can also be an electronic sensor, comprised of commercially available sensors such as coil or magnetoresistive sensors that will sense the change in magnet field when the magnet in the coupon transmitter changes position. The rate of corrosion can be easily computed if the time between the installation of the coupon and the failure of the coupon is known. If two or more coupons of different thickness are used, more information about the rate of corrosion can be determined. The magnetic field can change, because the magnet is physically displaced with any movement of the spring when the coupon fails, or the magnet rotates or moves in a known pattern (e.g., rotation or translation) as the coupon fails. The output of the receiver unit can be, transmitted via a wireless communication system such as a radio frequency (RF) tag to a computer located at another location for additional analysis or for archiving.

An advantage of the present invention is that it provides a safe method of measuring corrosion in a nuclear waste container, or a storage tank or piping containing corrosive fluids.

Another advantage of the present invention is that it provides a safe method of measuring corrosion inside a containment system without penetrating the walls of the containment system.

A further advantage of the present invention is that it provides a method of measuring corrosion a containment system without requiring electrical power.

A further advantage of the present invention is that it provides a method of measuring corrosion a containment system without removing, handling, inspecting, or assessing the condition of the corrosion coupons.

IN THE DRAWINGS

FIG. 14 is an illustration of the present invention implemented in a horizontal frame for monitoring the corrosion of the floor of an aboveground storage with a translation coupon-failure signal.

DETAILED DESCRIPTION OF THE PREFERRED EMBODIMENT

The method and several embodiments of the apparatus are illustrated for three applications of the present invention: (1) sealed containers storing nuclear materials; (2) an aboveground storage tank containing petroleum or other substances, both hazardous and non-hazardous (e.g., water); and (3) pipelines containing petroleum or other substances, both hazardous and non-hazardous. However, the present invention is applicable for many other applications. The present invention is applicable for any service environment in which a corrosion coupon can be used, including those environments comprised of liquids, gases, mixed-phase solutions, slurries, and radioactive materials. It is best implemented for containers, areas, or structures that are difficult, inexpensive, or inconvenient to access. For those skilled in the art, the method and the apparatuses described can be applied to a much wider range of corrosion problems.

Figure 1:
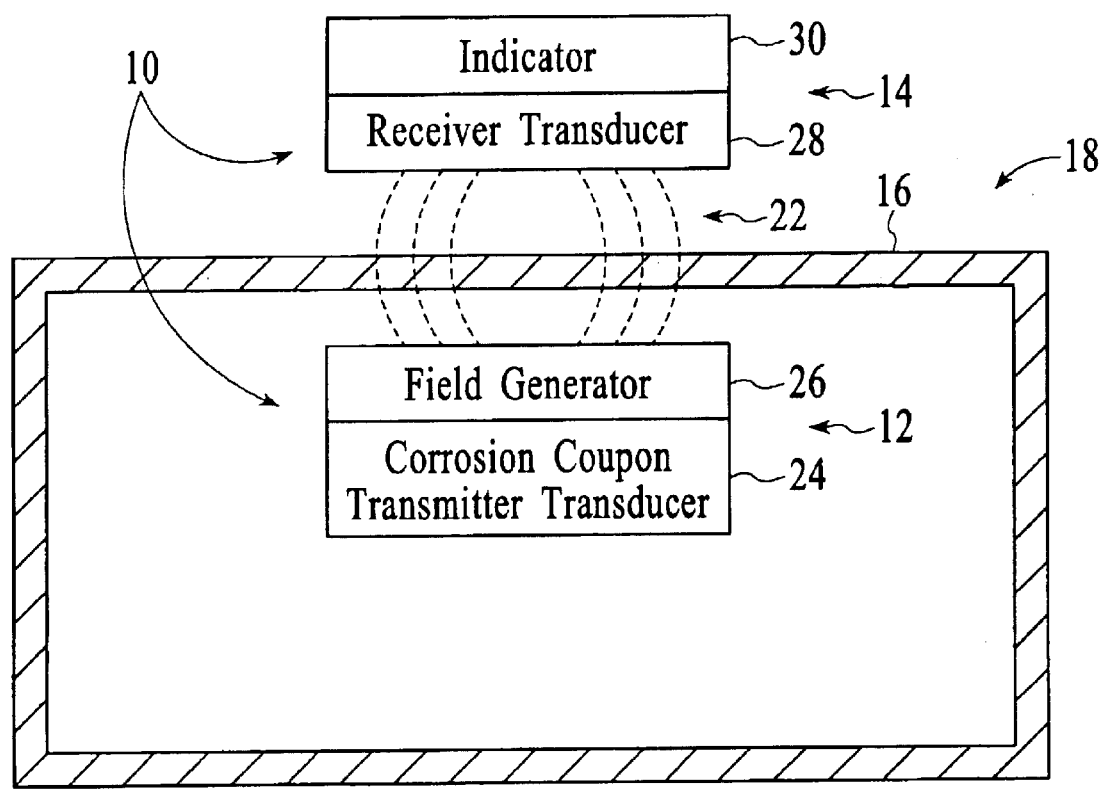
FIG. 1 is a block diagram of the preferred embodiment of the present invention.

The preferred embodiment of the method and apparatus of the present invention is illustrated in FIG. 1. It illustrates how the invention can be applied to a sealed container or a container in which penetrations are not desired, unsafe, or expensive to implement. According to the present invention, an apparatus 10 is provided for determining the corrosion of an environment inside a sealed container 18. The apparatus 10 includes a corrosion coupon transmitter apparatus 12 (or transmitter apparatus 12) that is separated from a receiver apparatus 14, by a wall 16 of the container 18. The container 18 wall 16 is preferably constructed of a non-magnetic or weakly magnetic material. For storage of nuclear waste material, the container is preferably constructed of stainless steel, a weakly magnetic metal. Other non-magnetic or weakly magnetic metals, plastics, and composite materials are also included in the spirit of the present invention. In addition, magnetic metals are also included in the spirit of the present invention.

The transmitter 12 is self contained and does not require any physical connections or holes through the wall 16 for communication to the receiver 14. The transmitter 12 is constructed to respond to the failure of the corrosion coupon 24 inside 20 of the container 18. The transmitter 12 includes a corrosion coupon 24 responsive to the environment and a magnetic field generator 26 to provide the magnetic field 22 with a characteristic indicative of the binary status of the corrosion coupon (either in an intact or failed condition). The characteristic may be a magnetic field orientation, the presence or absence of a detectable magnetic signal, or the strength of the magnetic field. The term "radiate" may be used in the following text and claims as a general term referring to the existence or creation of a magnetic field, even though in the case of a permanent magnet the field is not usually moving outward, but is static and therefore does not require an energy supply to sustain energy radiated from the magnet. The receiver 14 includes a receiver transducer 28 responsive to the field 22 to cause an indicator 30 to provide a communicative indication of the state of the corrosion coupon 24. The communicative indication can be any of various types, including display apparatus such as a needle and scale, or a digital read-out using LEDs, etc. The term "magnetic field generator" applies to any of the devices known by those skilled in the art for providing a magnetic field, and is preferably achieved using permanent magnets. The term "characteristic" applies to any property of a magnetic field that can be altered by movement (i.e., a change in position) of the magnet due to failure of a corrosion coupon. A particular and important embodiment of the present invention is the application of the disclosed apparatus to monitor for corrosion inside a container used for storage of radioactive material, including nuclear waste.

Figures 2A, 2B:
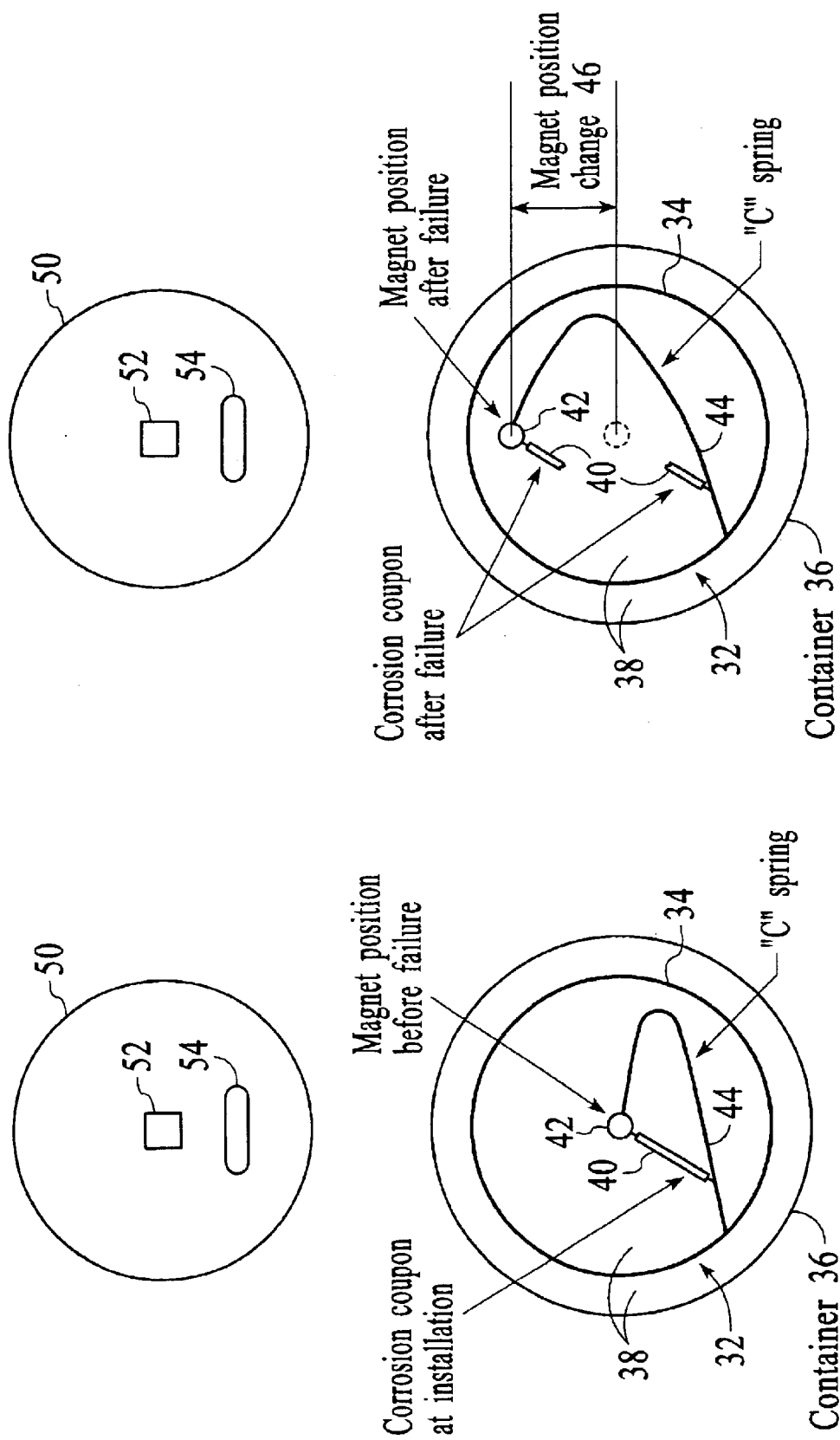
FIG. 2a is an embodiment of the present invention for a one-coupon system mounted on a C-spring that produces a change in the position of a magnet when the coupon fails.
FIG. 2b is an embodiment of the present invention for a one-coupon system mounted on a C-spring after the coupon fails.

FIG. 2 is a simplified illustration of a simple corrosion coupon transmitter 32 of an embodiment of the present invention. A transmitter 32 inside a container 36 is shown and includes a holder 34 for a corrosion coupon 40 and magnet 42 as the field generator. In this embodiment, a magnet 42 is secured to one end of a "C"-shaped spring 44 preferably made out of stainless steel or another non-magnetic material. The other end of the "C" spring would be attached to the inside of a frame 34 that allows direct communication between the coupon and the corrosive environment 38 in the container 36. For storage of nuclear materials, the steel container 36 would be made of stainless steel; for other types of stored materials, liquids, or gases, it can be made of other materials. A thin, narrow "ribbon" coupon 40 made out of the same material as the container would be welded across the ends of the spring in such a way that the "C" spring was held in tension (FIG. 2a). Being made of the same material as the container, the corrosion coupon 40 would be subject to the same corrosion effects as everything else within the sealed container 36; if the canister were corroding, the coupon would also be attacked and corrode. But being made of much thinner material than the sealed container itself, the corrosion would cause the coupon to fail first. When the coupon failed, the spring, being relieved of the tension, would expand 46 out to its equilibrium shape (FIG. 2b). This would translate the magnet 42 away from its in-tension position.

An external sensor 52, which is capable of detecting the change in the magnetic field produced when the coupon 40 fails (i.e., breaks), such as a Hall Effect device 52 or a magnetoresistive device 52, would sense the change in position of the magnet 46 and signal a corrosion-caused failure of the coupon. The external sensor is typically battery operated 54 and installed in a mounting device that can be positioned outside the container whose inside environment 38 is being monitored for corrosion. This change in the magnetic field would be an indication that corrosion was occurring in the container, In this case, the change in the magnetic field would be very close to binary in nature (absence or presence of a detectable magnetic field); that is, the output of the sensor would determine that the coupon 40 had failed or not.

Depending on the thickness and/or shape of the coupon 40, the coupon could give an earlier indication of corrosion than other techniques, including destructive testing. Furthermore, this invention would not require the containers to be destructively tested, radiographed, or even removed from their storage environment.

Figure 3A:
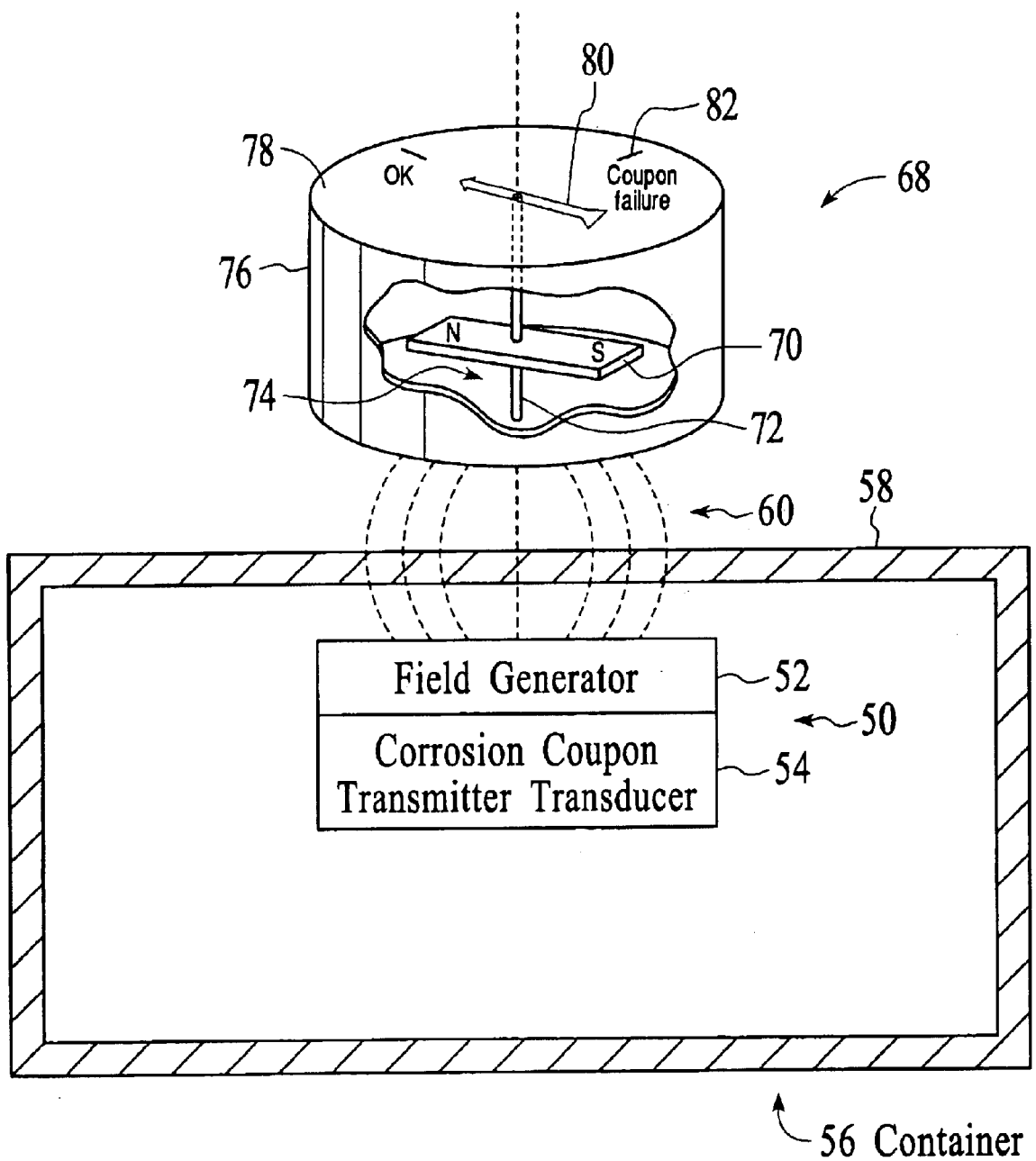
FIG. 3a is a mechanical embodiment of the receiver used to sense the magnetic field generated by the corrosion coupon transmitter positioned inside a containment system.
Figure 3B:
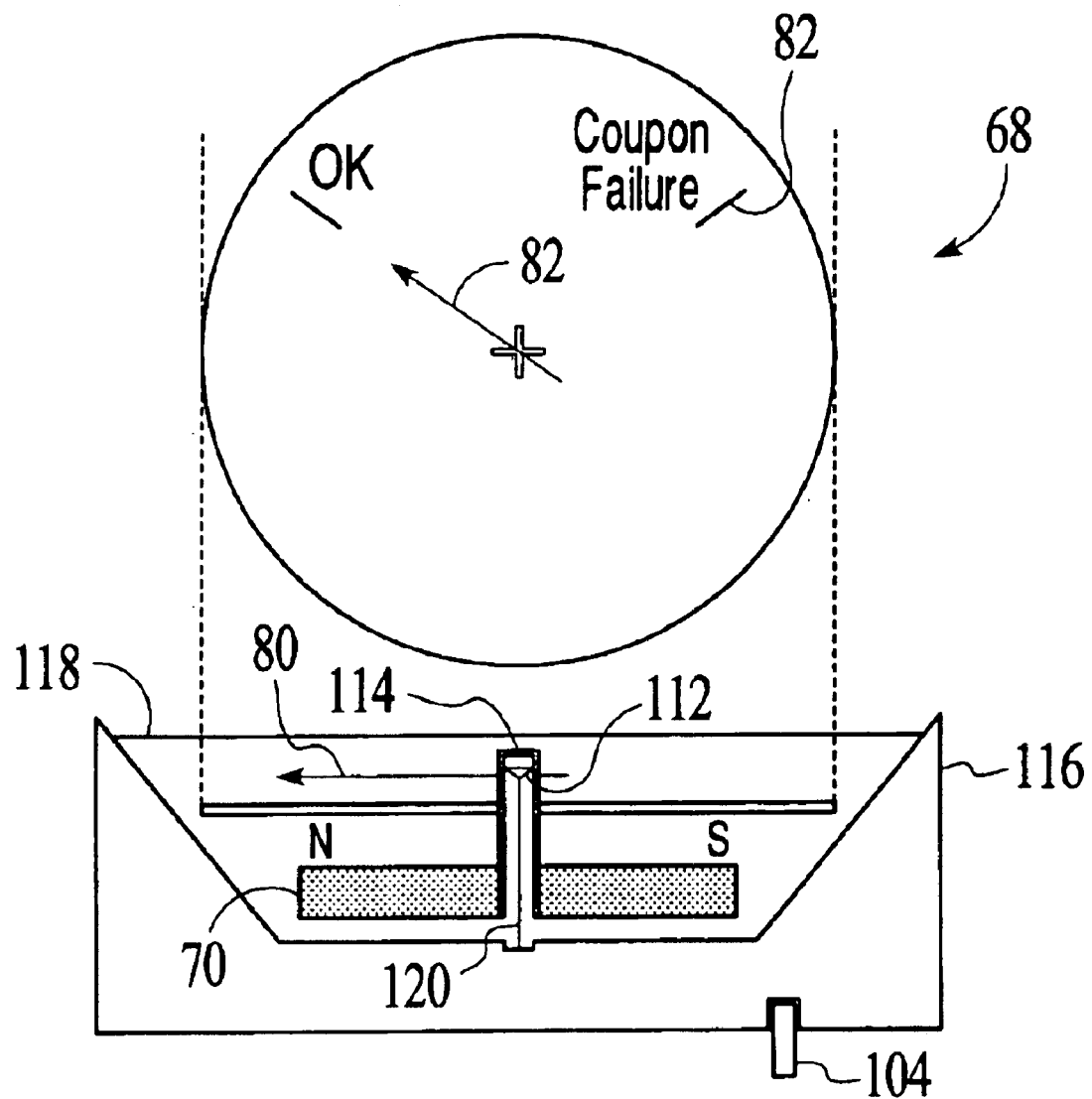
FIG. 3b shows an enlarged view of the mechanical receiver.

As shown in FIG. 3a, the receiver 68 could also be a mechanical system such as a compass-like measurement system where the position or alignment (pointing direction) of the needle 82 indicates the location of the magnet in the transmitter apparatus 50. FIG. 3a shows the receiver 68, container 56, and corrosion coupon transmitter 50. FIG. 3b shows an enlarged view of the receiver 68. The receiver apparatus 68 could be positioned close to the wall 58 of the container 56 within sensing range of the magnetic field 60 produced by the magnet 52 in the transmitter apparatus 50. The receiver has a magnet 70 attached to a pin 72 that is pivotally mounted to the base 74 of the receiver housing 76. The pin 72 extends upward through the top 78 and attaches to a pointer 80 for pointing to a calibrated scale 82 indicative of the failed or intact (OK) state of the coupon 54 in the container 56. The field 64 transmitted (radiated/extended) from the magnet 52 of transmitter 50 extends to the wall 58 and passes through the wall 58 without being altered if the wall 58 is not magnetic. If the wall is magnetic, the field aligns magnetic domains in the magnetic wall, and the magnetized wall portion 58 then radiates-extends a corresponding magnetic field exterior through the container 56. The magnet 70 of the receiver, being free to rotate, then aligns itself with the field extended by the magnet 62, which is in a position dependent on the state (failed or intact) of the corrosion coupon 40. The resulting orientation of the magnet 70 is transferred via pin 72 to pointer 80 to point at the scale 82 indicating whether or not the coupon has failed.

The apparatus of FIG. 2 is illustrative of a very simple embodiment of the present invention. Other transmitter and receiver constructions for responding to the state of one or more coupons in the corrosive environment and transferring a magnetic indication of a value of the property through a boundary, which may also have magnetic properties, and detecting the magnetic field and displaying a parameter value indication will be apparent to those skilled in the art, and these are included in the spirit of the present invention.

Figure 4A:
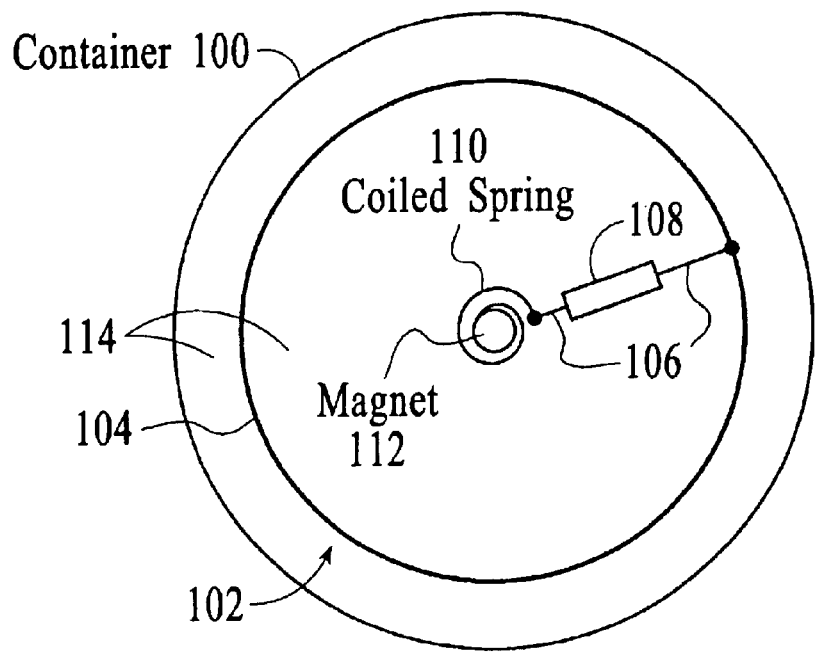
FIG. 4a is an embodiment of the present invention for a one-coupon system that produces a rotation change in the position of a magnet when the coupon fails.
Figure 4B:
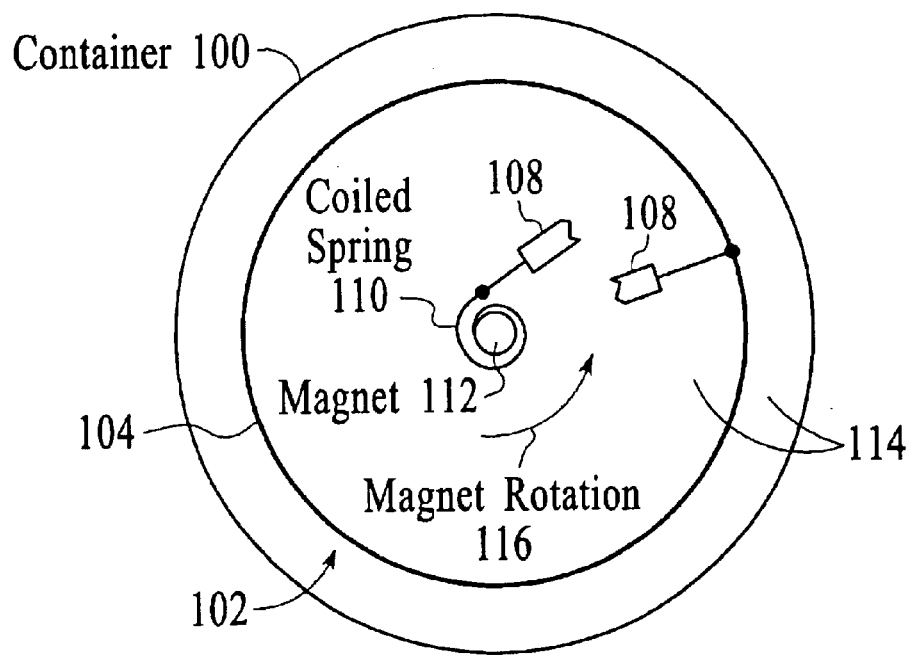
FIG. 4b is an illustration of an embodiment of the present invention foe a one-coupon system after the coupon fails.

There are many variants of the present invention. The "right" design of apparatuses based on the present invention would depend on what potentially corrosive environment needs to be measured and how accurately or precisely it needs to be measured. As an example, the "C" spring could be replaced by a coiled spring; in this case, the failure of the coupon would be indicated as a change in the rotation angle of the magnet. FIG. 4 is a simplified illustration of a transmitter 102 in a sealed container 100. A coiled spring 110 is mounted to the holder 104, which bottom is open to the environment 114 of the container 100. A magnet 112 is attached to the coiled spring 110 in such a way that it will rotate as the coiled spring 110 rotates. Here, the coupon 108 failure would cause a pre-determined rotation of the magnet 112 that would be measured by the receiver such as the ones shown in FIGS. 1–3. Coupons (ribbons, wires, or rods) of incrementally increasing thickness could be mounted to the "C" or "coiled spring" in such a way that as each failed in turn with continued corrosion, the corrosion rate could be estimated. FIG. 4b illustrates the rotation 116 of the magnet after the coupon fails.

Figure 5A:
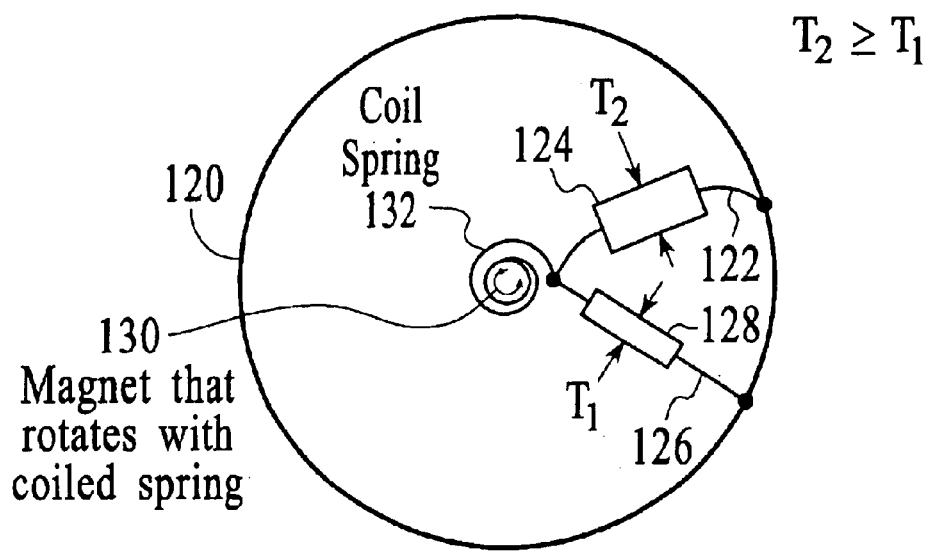
FIG. 5a is an illustration of an embodiment of the present invention for a two-coupon system that produces a rotational movement of the magnet when a coupon fails.
Figure 5B:
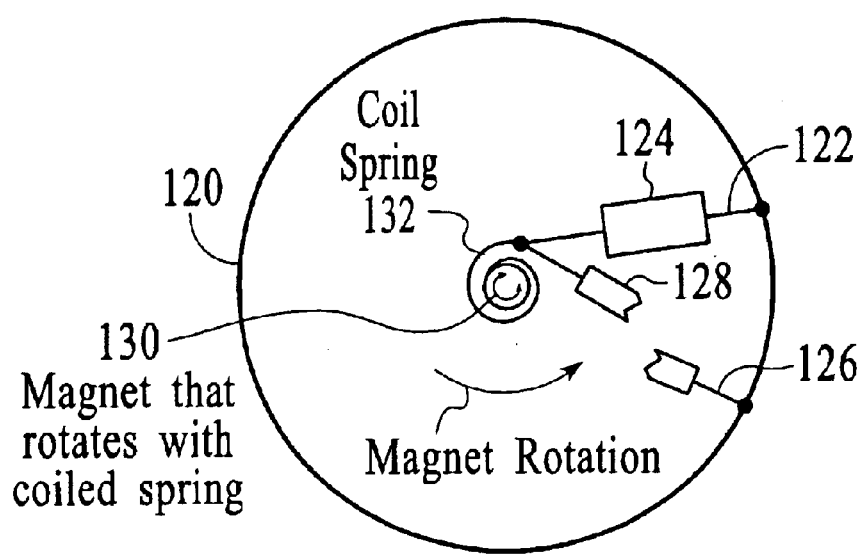
FIG. 5b is an illustration of an embodiment of the present invention for a two-coupon system after one of the coupons fail.

FIG. 5 illustrates a two-coupon transmitter similar to the transmitter described in FIG. 4. FIG. 5a illustrates the position of the coiled spring 132 and the magnet 130 before any of the coupons 124, 128 fails. When coupon 128 fails, as shown in FIG. 5b, the coiled spring 132 rotates, which in turn rotates the magnet 130, which changes the magnetic field radiated to the receiver. Each failed coupon would cause the magnet 130 to rotate (or translate) a pre-determined distance; a line of magnetic sensors in the receiver would measure the incremental translation and indicate which of the coupons had been broken. The receiver could also consist of a electronic coil or magnetoresistive receiver shown in FIG. 2 or the mechanical compass-like receiver illustrated in FIG. 3. The rotation angle of the magnet 130—measured by the receiver—would be a measure of the number of the coupons that had been corroded.

For nuclear corrosion measurements, the magnet 130 would preferably be a samarium-cobalt (SmCo) magnet, because it has several advantages. First, it has a very high magnetic strength; this allows a small magnet to send out a large and easily detectable magnetic field. Second, SmCo is the magnet material most commonly used in radiation environments where high field strength is needed—it resists demagnetization due to radiation-induced depolarization of the magnetic dipoles.

Figure 6:
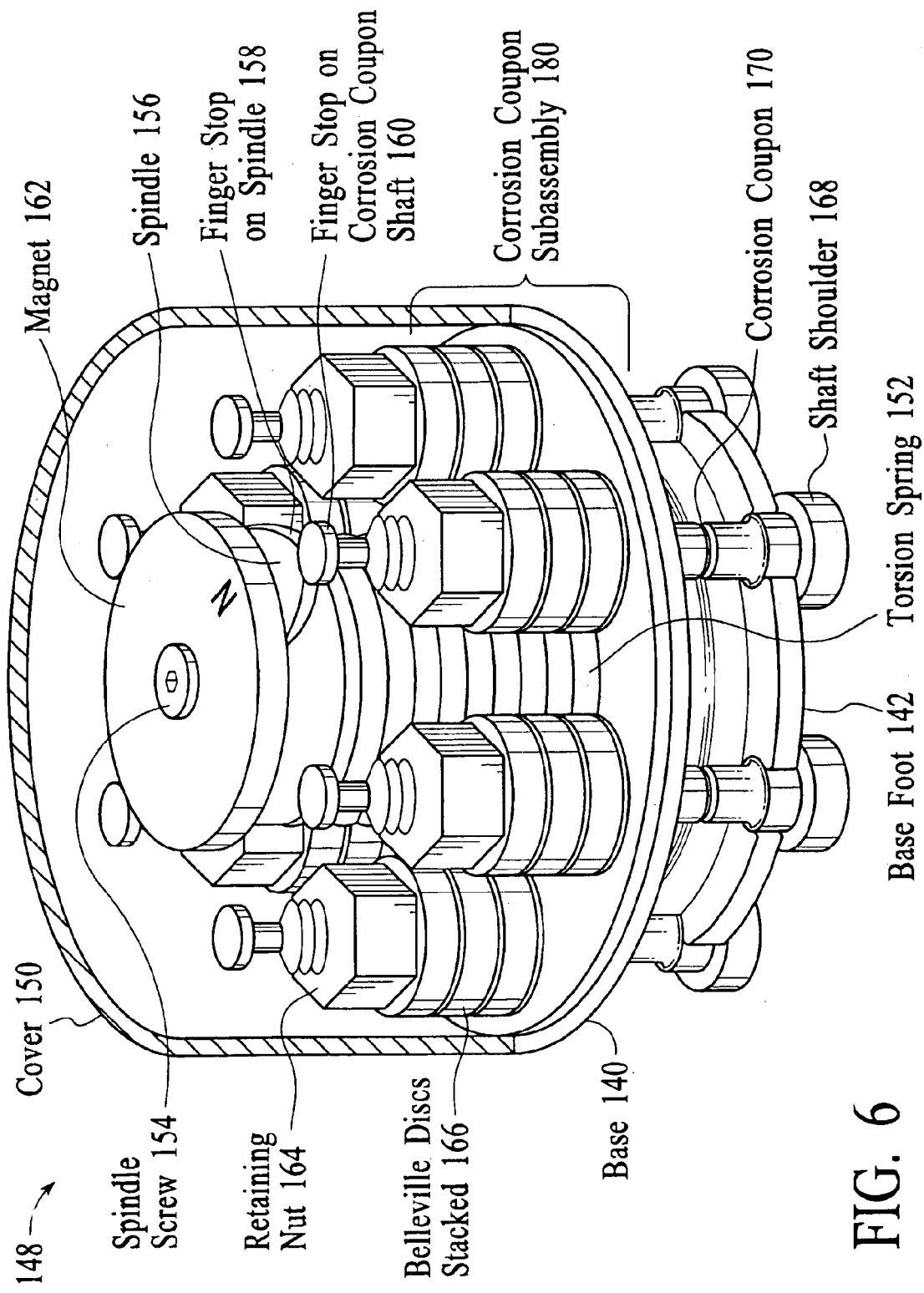
FIG. 6 is an illustration of an embodiment of the present invention for a multiple-coupon system mounted on a coil spring that produces a rotational movement of the magnet when the coupons fail.

A simplified illustration of another embodiment of the present invention with a coiled spring is shown in FIG. 6. In this embodiment, the corrosion coupon can be placed under a pre-determined stress loading, which is required for estimates of stress-corrosion cracking. FIG. 6 illustrates a six-coupon transmitter 148. However, the transmitter can be implemented with as few as one coupon or as many as is physically possible within the transmitter.

FIG. 6 illustrates the embodiment in a three-dimensional view of the transmitter 148. The magnet 162 is mounted onto a ball bearing-supported spindle 156 that includes a finger 158. The spindle finger 158 touches a finger stop 160 that is part of a corrosion coupon 180 subassembly, discussed below. The base of the transmitter 148 secures one end of a torsion spring 152 while the other end is attached to the rotary assembly causing the spindle assembly to 156 (attempt to) rotate. For a corrosion coupon 170 that is intact (i.e., that has not "failed"), the rotation of the finger 158 and magnet 162 is inhibited by the presence of the finger stop 160. The base of the transmitter 140 also supports the bottom end of the corrosion coupon subassemblies 180.

When sufficient corrosion occurs, a coupon 170 fails and the coupon separates at the specimen region—the location of the subassembly where the coupon is designed to fail when it corrodes and weakens. When the coupon fails, a set of Belleville springs 166 within the case causes the upper portion of the coupon assembly to "pop up". This moves the finger stop 160 out of the way of the finger 158 on the spindle allowing the spindle assembly 156 with the magnet 162 to rotate to the next finger stop 182. The receiver, as illustrated in FIGS. 1–3 measures the rotation of the magnet signaling failure of that particular coupon. As illustrated in the figure, multiple coupons can be employed, each with a decreasing stress applied in order to clearly establish a corrosion rate of the process occurring inside the container.

Figure 7:
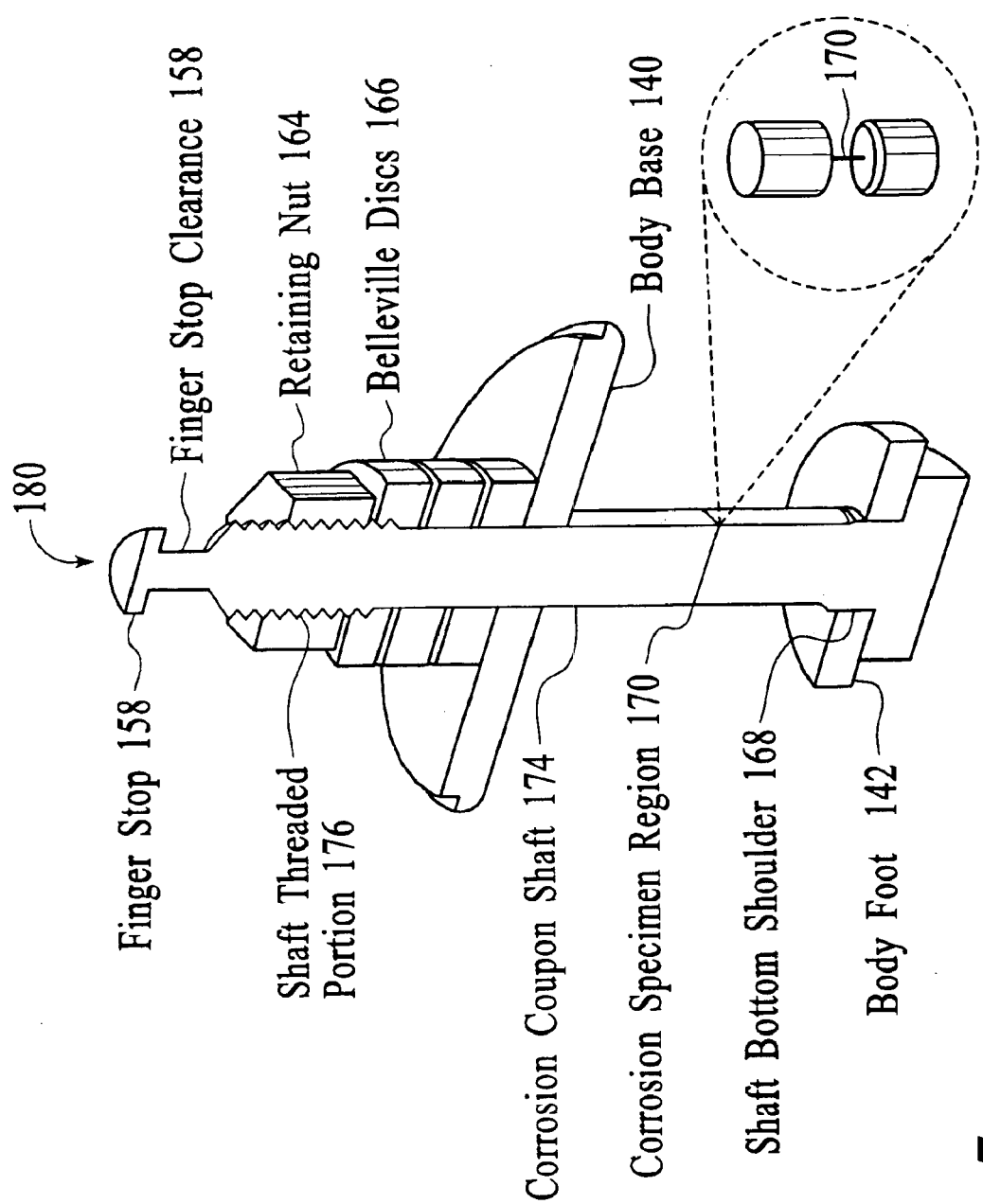
FIG. 7 is an illustration of the corrosion coupon subassembly.

The details of the corrosion coupon subassembly 180 are shown in FIG. 7. This subassembly (made from stainless steel or any other high-tensile material designed to measure the corrosion process) has a one-piece, partially threaded, corrosion coupon shaft 174 that includes a region for the corrosion coupon 170. A stack of Belleville washers 174 are compressed against the base 140 of the transmitter with a tensioning nut 164; this provides the stress to the specimen region and allows the finger stop 158 to pop up when the corrosion coupon 170 fails. The top end of the shaft 174 incorporates the finger stop 158 and the bottom end of the shaft 174 has a shoulder 168 that fits into a foot 142 at the bottom of the body. Only the lower portion of the corrosion coupon—that portion of the subassembly containing the specimen region—is exposed to the corroding environment.

Figure 8A:
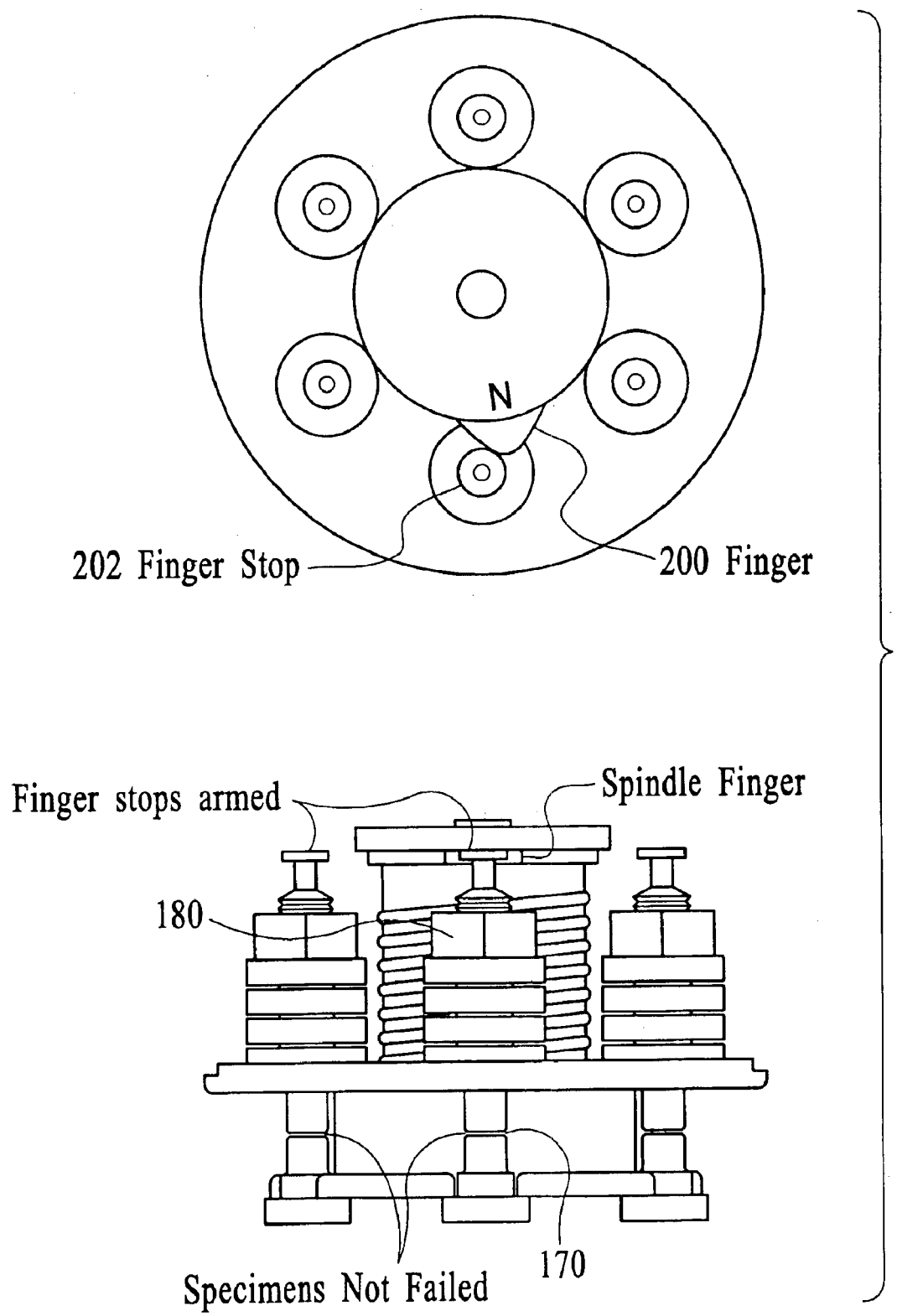
FIG. 8a is an illustration of an embodiment of the present invention for, a multiple-coupon system that produces a rotational movement of the magnet when the coupons fail.

The transmitter illustrated in FIG. 6 incorporates six corrosion coupons, each arranged at 60-degrees intervals. FIG. 8a shows the corrosion mechanism in the "armed" or "ready" position where the corrosion coupon 170 on the corrosion coupon subassembly 180 has not yet failed. As noted above, the specimen region of the mechanism is external to the case and is exposed to the corrosive material; this allows the coupon specimen to experience the same corrosion processes being experienced by the container being measured.

Figure 8B:
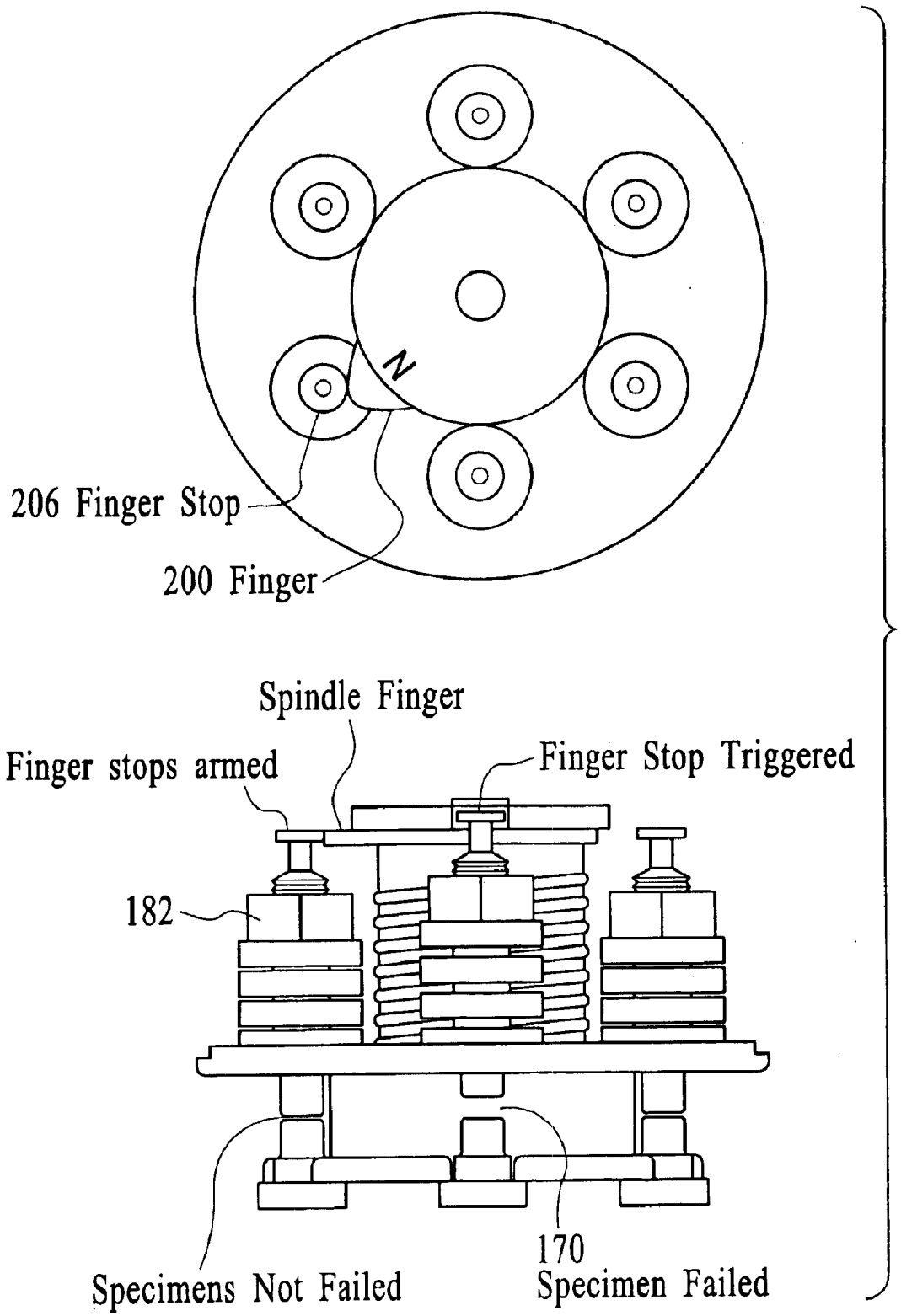
FIG. 8b shows the rotational change of the magnet after the first corrosion coupon fails.

In the "armed" or "ready" state, as illustrated in FIG. 8a, the finger 200 on the torsion-spring-loaded spindle assembly (i.e., coiled spring) is prevented from rotating by the interference of the finger stop 202 portion of the corrosion coupon shaft. As shown in FIG. 8b, when the corrosion coupon 170 fails, the finger stop 202 "pops up" allowing the spindle finger 200 to pass by the finger stop 202 clearance section to the next corrosion coupon subassembly 182 where it is stopped by the finger stop 206.

Each of the six coupons illustrated in FIGS. 6 and 8, which are arranged around the periphery of the case interior, may be under different stress and will be arranged in the order that the coupons are expected to fail. These coupons could be spaced at uniform 60-degree intervals. However, a non-uniform spacing interval can also be used such that there is a unique relationship between the coupon and the angular change observed between coupon failures. This type of spacing arrangement ensures that when a coupon fails, the measured angular change will be an indicator of which coupon failed. This arrangement assures that the corrosion process can continue to be monitored and quantified, even if the zero-coupon index position is lost.

The stress applied to the coupon section is strictly a function of the applied force imposed by the Belleville discs and the cross-section of the corrosion coupon. Either one may be varied to achieve the desired stress. For example, a stack of seven fully compressed, off-the-shelf Belleville washers will exert a force of about 430 pounds. For this force, the applied stress can be simply determined from the cross-sectional area of the specimen region. Table 1 shows the stress (in psi) that can applied, for various diameters of a circular-shaped specimen region.

TABLE 1

| Specimen diameter required for specified stress at 430# force | | | | | |
| --- | --- | --- | --- | --- | --- |
| Stress (psi) | 30,000 | 25,000 | 20,000 | 15,000 | 10,000 |
| Diameter (in.) | 0.135 | 0.148 | 0.165 | 0.191 | 0.234 |

Figure 9A:
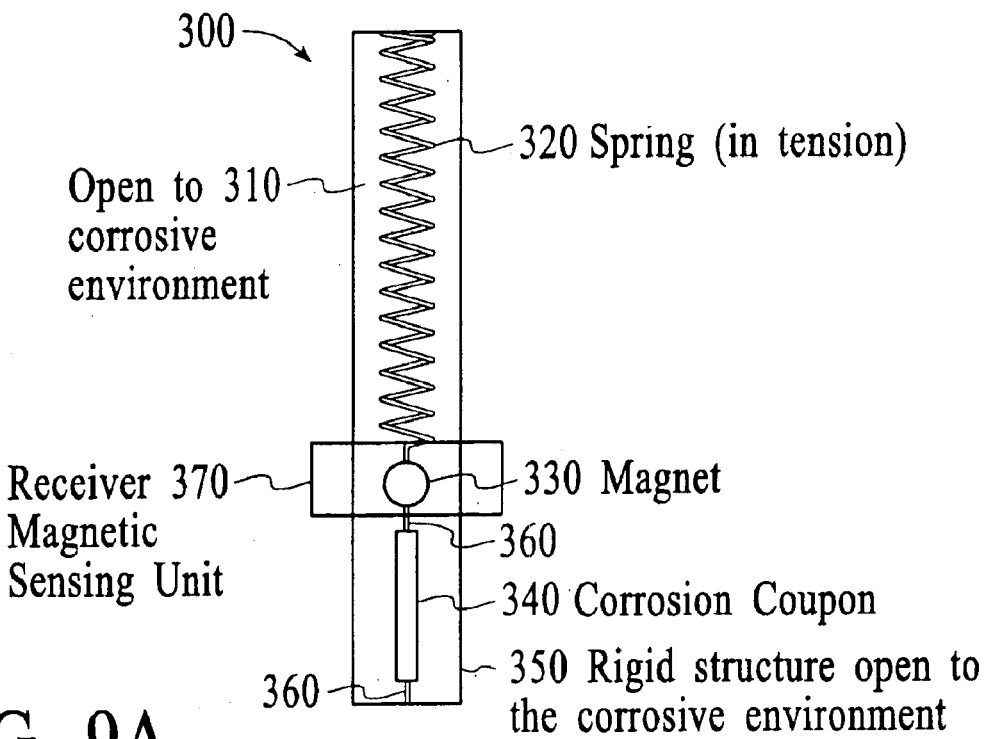
FIG. 9a is an illustration of an embodiment of the present invention for a one-coupon system that produces a translational movement of the magnet when the coupon fails.
Figure 9B:
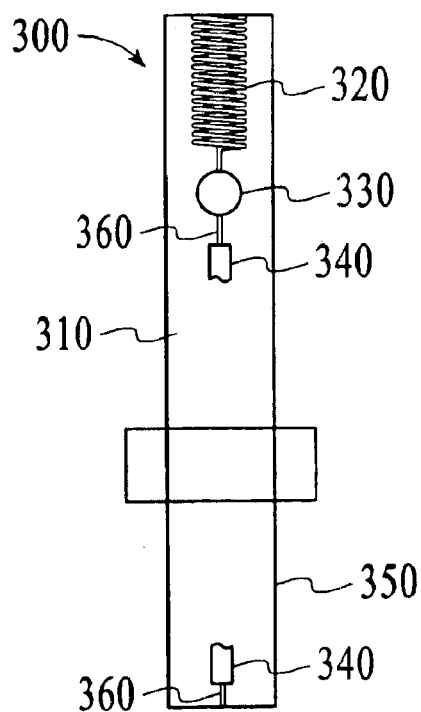
FIG. 9b is an illustration of an embodiment of the present invention for a one-coupon system after the coupon fails.
Figure 10A:
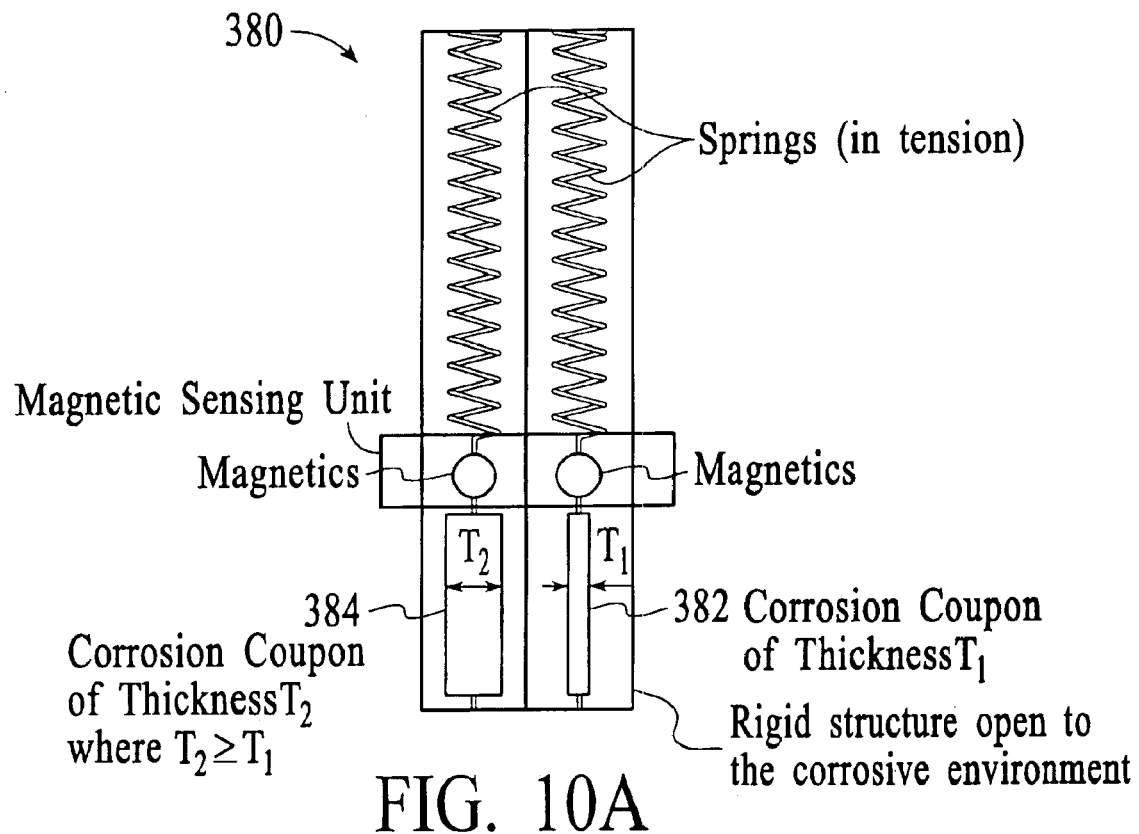
FIG. 10a is an illustration of an embodiment of the present invention for a two-coupon system that produces a translation movement of the magnet when a coupon fails.
Figure 10B:
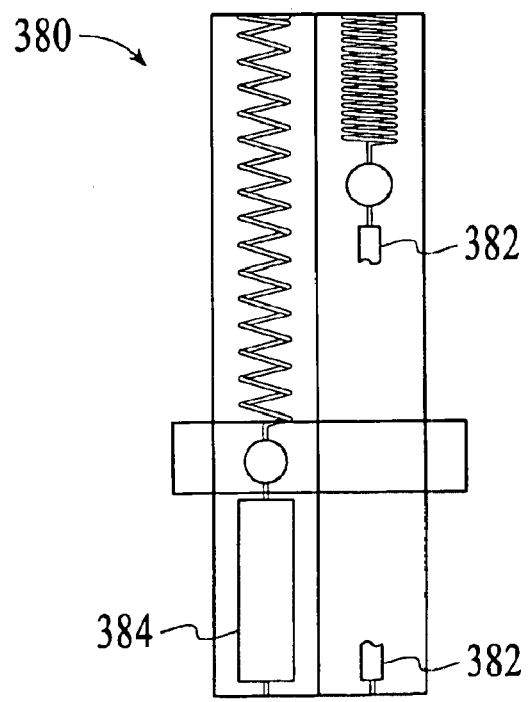
FIG. 10b is an illustration of an embodiment of the present invention after one of the coupons fails.
Figure 11:
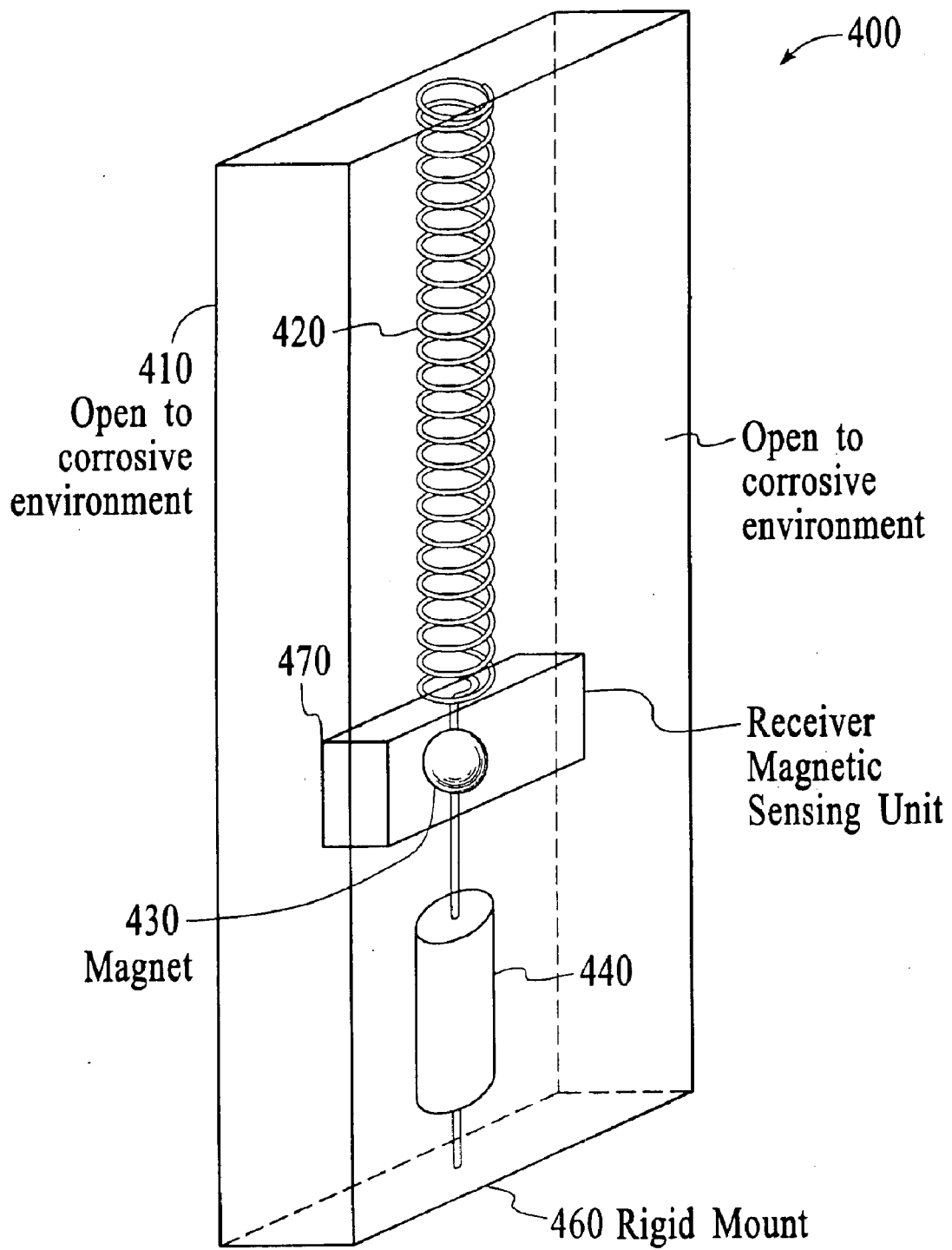
FIG. 11 is an illustration of an embodiment of the present invention for a one-coupon system in a rigid structure entirely open to the service environment that produces a translation movement of the magnet when the coupon fails.

FIGS. 9–11 are simplified illustrations of alternative embodiments of the present invention where a coupon failure results in a translation (rather then rotation) of the magnet. The transmitter 300 in FIG. 9 results in the same information and has the same functionality as the rotational transmitters illustrated in FIGS. 4–8. The transmitter 300 is comprised of a spring 320 attached to a rigid structure 350 open to the service environment 310, and a corrosion coupon 340 attached by a wire or rod 360 to the mounting structure 340 and the magnet 330. A receiver with a magnetic sensing device 370 is located above the transmitter 300 in the "armed" or "ready" position of the magnet. When the corrosion coupon fails, as illustrated in FIG. 9b, the spring 320 pulls or translates the magnet away from its "armed" or "ready" position. The magnetic sensing system in the receiver 370 can easily detect the decrease in the magnetic field that occurs when the magnet is pulled away from its "armed" or "ready" position. The receiver could also be positioned where the magnet will come to rest after the coupon fails. It that position, it will sense an increase in the magnetic field.

FIG. 10 illustrates an embodiment of the present invention shown in FIG. 9, but with two corrosion coupons 382, 384, in which one of the coupons 382 is thinner than the other coupon 384. FIG. 10a illustrates the transmitter in the "armed" or "ready" position, and FIG. 10b illustrates the transmitter after the thinner coupon 382 has failed. Clearly, a multiplicity of coupons of different designs and thicknesses can be used. For the clearest interpretation, the coupons should be installed in the transmitter 380 in the order they are expected to fail. FIG. 11 illustrates an embodiment of the transmitter 400 of the present invention shown in FIG. 9, but with a rigid frame 460 open to the environment 410 on all sides holding the spring 420, magnet 430, and corrosion coupon 440. The receiver 470 will detect the presence or absence of a magnetic field that corresponds to the failure status of the coupon 440.

Figure 12:
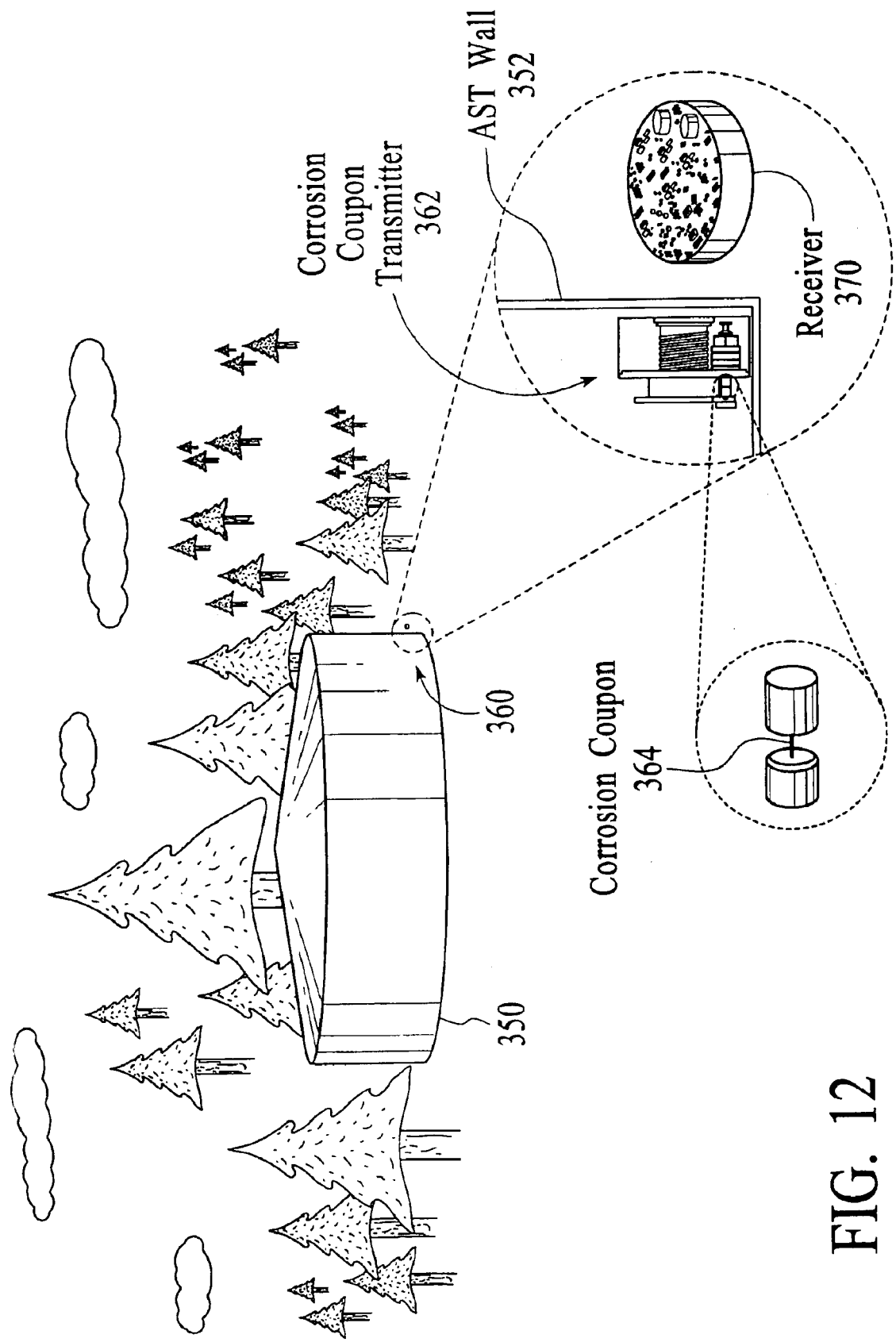
FIG. 12 is an illustration of the use of the present invention for monitoring corrosion in an aboveground storage tank.

FIG. 12 illustrates the application of the transmitter shown in FIG. 6 in an aboveground storage tank. The main difference between this application and the nuclear container application is that a storage tank is typically constructed of steel, a magnetic material, and the nuclear containers are typically constructed of stainless steel, a weakly magnetic material. The receiver can detect the magnetic field changes even for magnetic materials, because the strength of the magnetic field is strong and localized due to the rotation (or translation) of the magnet in the transmitter. In FIG. 12, the transmitter and receiver pair 360 is located on or near the wall of the tank. The transmitter 362 is located inside the tank and is submerged in the fuel. Only the corrosion coupon 364 is immersed in the fuel environment. The receiver 370 is located on the outside part of the tank wall 352. The receiver shown in FIG. 12 includes a battery, a magnetoresistive chip, and a wireless communication system.

Figure 13A:
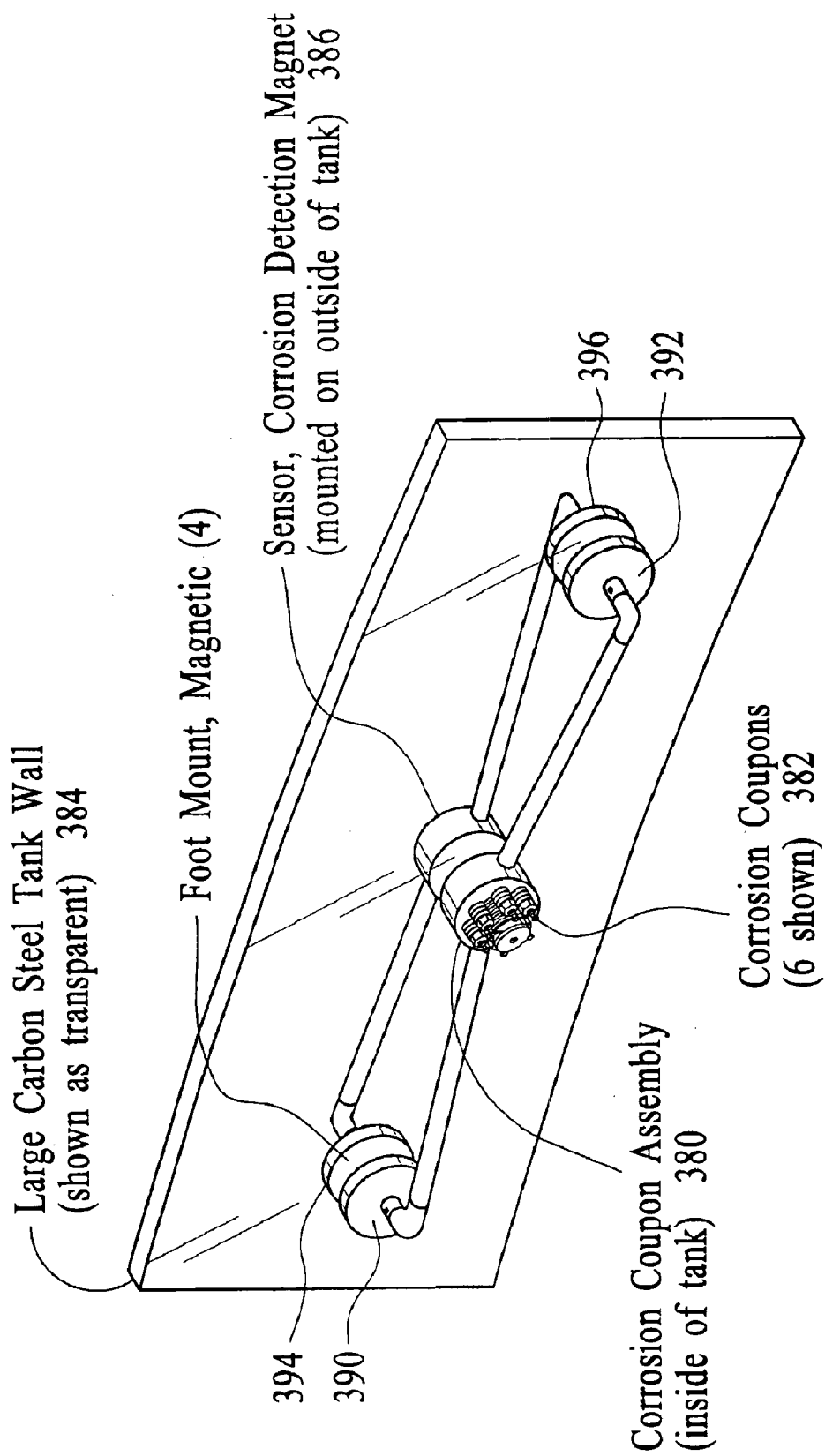
FIG. 13 is an illustration of the present invention implemented in a magnetic mounting system for monitoring the corrosion in an aboveground storage tank.
Figure 13B:
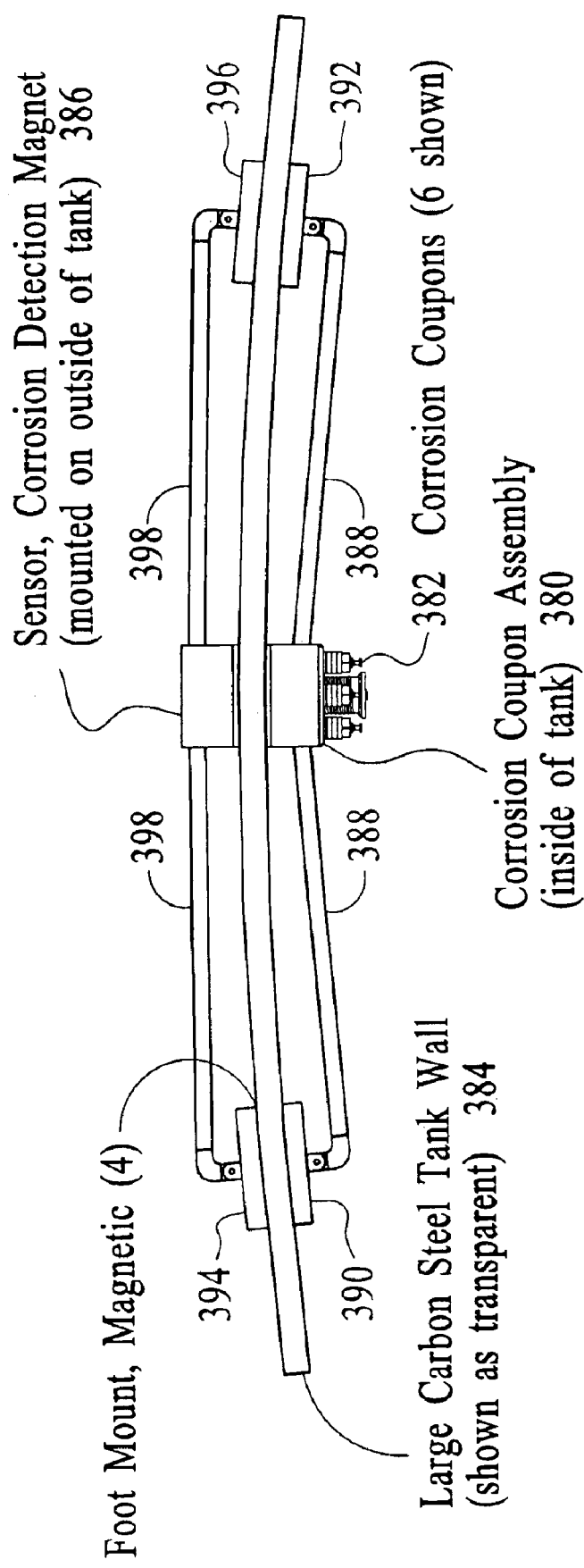

FIG. 13 is a simplified illustration of an embodiment of the present invention for monitoring corrosion of the inside walls or floor of an aboveground storage tank. In this case, a magnetic mounting system is used to mount the transmitter on the inside wall of the tank and a similar mounting system is used to mount the receiver on the outside of the tank. The receiver 386 and the transmitter 380 are aligned so that any movement of the magnet inside the transmitter 380 can be properly interpreted. The receiver is comprised of a battery, an electronic magnetic sensing chip, a battery and a wireless communication system to transmit the measured data to a computer. The receiver may also include a digital display. The receiver could also be simplified by replacing the electronic receiver by a mechanical one similar to the one shown in FIG. 3.

FIG. 14 is an illustration of an apparatus 510 for monitoring the corrosion of the floor of an aboveground storage tank 500. The transmitter 520 and the receiver 580 are positioned on opposite sides of the tank wall 502. The transmitter 520 is comprised of a corrosion coupon subassembly 540 that is very similar to the one illustrated in FIGS. 4–8. The main difference is that the magnet 564 is attached to a long rod 550 that separates the corrosion coupon subassembly 540 from the magnet 564. The corrosion coupon subassembly 540 is comprised of the a base foot 562 that hold the assembly 540 at the base, Belleville washers 560 putting the assembly under compression, a nut 558 located on a threaded rod 556 to anchor the subassembly at the top, and a corrosion coupon 570. The couplings 554 and 552 are only used if the rod 550 is long or needs an adjustment in length. The assembly 542 comprised of the corrosion coupon subassembly 540, rod 550, and magnet 564 is positioned in a mounting frame 530 that is open to the fuel environment and rests on the bottom floor of the tank. The distance between the magnet 564 and the tank wall 502 controls the strength of the magnetic field that needs to be sensed by the receiver 580. In the "armed" or "ready" position before the corrosion coupon 570 has failed, it is desirable that the magnetic field being sensed by the receiver be small (negligible). The number of Bellville washers can be varied so that the magnet will move close enough to the tank wall 502 and receiver 580 when the corrosion coupon 570 fails to produce a strong and very detectable magnetic signal at the receiver 580. While not explicitly illustrated in FIG. 14, the internal parts of the corrosion coupon subassembly can be enclosed in a sealed container, leaving only the corrosion coupon exposed to the fuel environment.

An array of transmitters and receivers, like the transmitter 520 and receiver 580 shown in FIG. 14, can be inserted into the tank with different coupon stresses and thickness to give the same information as the cylindrical transmitter illustrated in FIG. 6. The corrosion coupons for an aboveground storage tank application will be developed with different diameters to detect when certain levels of corrosion have occurred; these diameters should be selected to identify when certain levels of maintenance, repair or replacement of the aboveground storage tank need to be performed. The first corrosion coupon would have a small diameter and be designed to break in a short period of time if active corrosion in the tank is occurring. The fifth or sixth corrosion coupon would indicate that the thickness of the tank wall or floor is sufficiently thin that replacement of the aboveground storage tank or major sections of the aboveground storage tank may be necessary.

Figure 15:
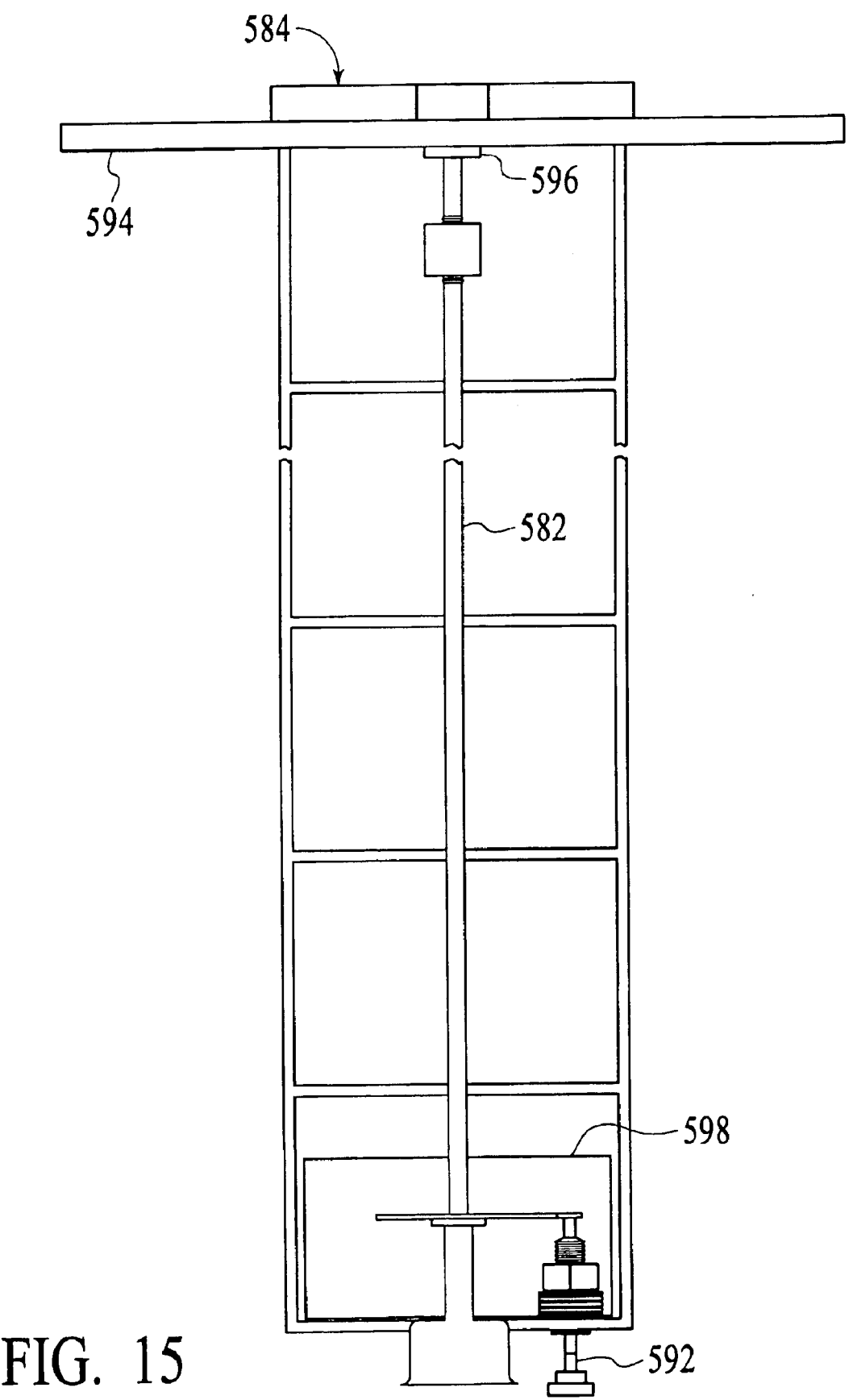
FIG. 15 is an illustration of the present invention implemented in a horizontal frame for monitoring the corrosion of the floor of an aboveground storage tank with a rotational coupon-failure signal.

FIG. 15 illustrates a rotational implementation of the transmitter 590. The transmitter is similar to the one illustrated in FIG. 6, except the transmitter 590 magnet 596 is located outside the enclosed portion of the transmitter 598 and on the end of the extension rod 582 near the tank wall 594 and the receiver 584 mounted on the tank wall 594. The corrosion coupon 592 is located away from the wall 594 and closer to the center of the tank. Multiple corrosion coupons can be implemented in the transmitter 590, as illustrated in the transmitter shown in FIG. 6.

For all embodiments of the present invention, if the magnet movement is sufficient, the receiver only needs to be able to detect the presence of absence of the signal. The location of the received signal, whether it is due to a translation, or rotation, is indicative of which corrosion coupon failed. By knowing the time between failures of the coupons, the thickness and loading of each coupon, both the amount and rate of corrosion can be determined and used to assess the life cycle of the structure or containment system.

Figure 16:
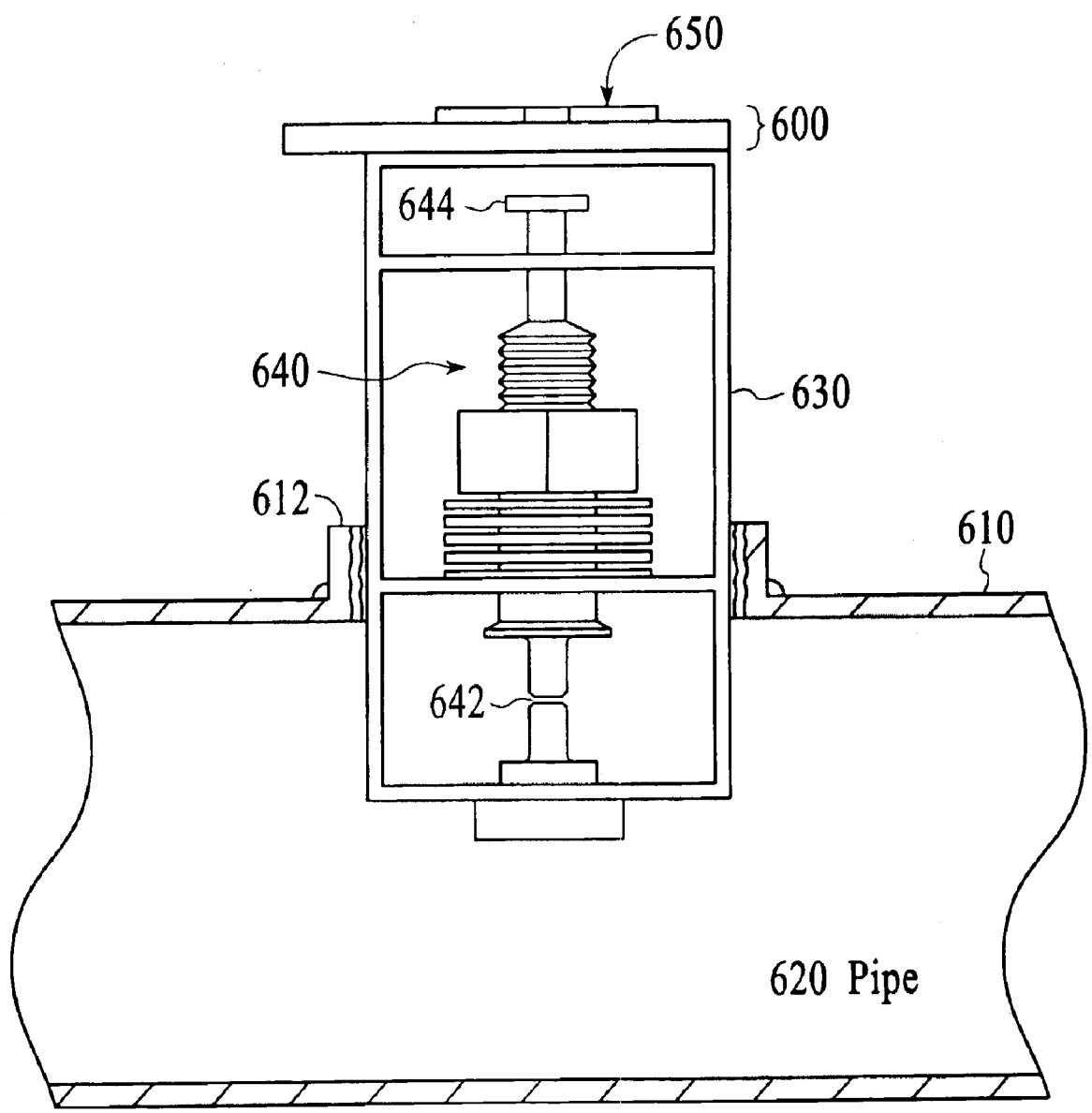
FIG. 16 is a simplified illustration of an embodiment of the present invention for measuring corrosion inside a pipe.

FIG. 16 is an illustration of a simplified drawing of an apparatus 600 for a pipe. The corrosion coupon subassembly shown in FIG. 7 is attached to the pipe in such a way that the corrosion coupon is positioned in the pipe fluid. The transmitter 630, with the corrosion coupon subassembly 640 and receiver 650, is threaded into the pipe 610 through a special coupling 612 that is welded onto the pipe. The transmitter 640 and receiver 650 pair 600 is very similar to the embodiment shown in FIG. 14, except the rod 550 and couplings 554, 552 extending the rod in FIG. 14 have been removed, and the received is positioned on the top of the transmitter 640 than on the wall separating the tank environment from the ambient air environment. The transmitter 640 works identically to the transmitter illustrated in FIG. 14. For pipe applications, the part of the transmitter 640 subject to the ambient air environment outside the pipe should be enclosed in a small housing.

Although the present invention has been described above in terms of a few specific embodiments, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. A method for determining the corrosion of a material in an environment using a corrosion coupon placed in the same environment, comprising the steps of:
   (a) placing said corrosion coupon in said environment;
   (b) sensing the failure of said corrosion coupon, wherein said failure is indicated by a movement of a magnet, creating a magnetic field which may be sensed without effecting said material;
   (c) sensing said magnetic field, wherein said magnetic field has a characteristic indicative of said failure, thereby producing a measurable external magnetic field at a distance from said corrosion coupon; and
   (d) responding to said external field to display an indication of said failure.

2. A method as recited in claim 1, wherein said method measures the amount of corrosion because the physical condition of the corrosion coupon is known before the coupon is inserted into said environment.

3. A method as recited in claim 2, wherein said method measures the rate of corrosion because the time to failure while in said environment is determinable.

4. A method as recited in claim 1, wherein the failure of said coupon is determined without penetrating a wall separating the location of said coupon from the location of said display.

5. A method as recited in claim 1 wherein said method uses a plurality of corrosion coupons.

6. A method as recited in claim 1 wherein said material to be monitored for corrosion is located in a radioactive environment containing an element selected from the group consisting of plutonium and uranium.

7. A method as recited in claim 1 wherein said magnet is moved by a spring attached to said coupon that is in compression until the coupon fails.

8. A method as recited in claim 7 wherein said spring applies a compressive force to said coupon.

9. A method as recited in claim 1 wherein said magnet is moved by a spring attached to said coupon that is in tension until the coupon fails.

10. A method as recited in claim 1 wherein said spring applies a tension force to said coupon.

11. A method as recited in claim 1 wherein said magnet is moved by Belleville washers under compression and applying stress to said coupon until said coupon fails.

12. A method as recited in claim 1 wherein said magnet is moved by Belleville washers under tension and applying stress to said coupon until said coupon fails.

13. A method as recited in claim 1 wherein said responding includes a magnet positioned exterior to said container aligning itself with said exterior magnetic field.

14. A method as recited in claim 1 wherein said responding includes at least one coil that can be used to sense said exterior magnetic field.

15. A method as recited in claim 1 wherein said responding includes a magnetoresistive device that can be used to sense said exterior magnetic field.

16. An apparatus for determining the corrosion of a material in an environment, using a corrosion coupon placed in the same environment, comprising:
   (a) transmitter apparatus for placement in the environment containing said material, including
      (i) a corrosion coupon mounting system with at least one with corrosion coupon;
      (ii) a transducer apparatus responsive to the position of each coupon to provide a corresponding position of a mechanical element;
      (iii) a transmitter magnet attached to each element for radiating a magnetic field characteristic corresponding to the position of each element, said magnetic field including an external magnetic field component that can be sensed at a distance from said element;
   (b) receiver apparatus for placement at a distance from the transmitter apparatus, said receiver apparatus including
      (i) receiver magnetic field sensing apparatus that measures a detectable characteristic of said external field component;
      (ii) a display apparatus responsive to a position of said receiver magnet to provide an indication of said position.

17. An apparatus as recited in claim 16 wherein said receiver magnetic field sensing apparatus includes a receiver magnet that aligns with said external field component.

18. An apparatus as recited in claim 16 wherein said display apparatus is a mechanical display.

19. An apparatus as recited in claim 16 wherein said display apparatus is a needle gauge.

20. An apparatus as recited in claim 16 wherein said display apparatus is an electronic display.

21. An apparatus as recited in claim 16 wherein said transducer apparatus produces a rotational movement in response to a failure of said corrosion coupon.

22. An apparatus as recited in claim 16 wherein said transducer produces a translational movement in response to a failure of said corrosion coupon.

23. An apparatus as recited in claim 21 wherein said receiver apparatus senses the external magnetic field of the rotational movement produced by said transmitting apparatus.

24. An apparatus as recited in claim 22 wherein said receiver apparatus senses the external magnetic field of the translational movement produced by said transmitting apparatus.

25. An apparatus as recited in claim 16 wherein said receiver apparatus is a coil that senses said external magnetic field component.

26. An apparatus as recited in claim 16 wherein said receiver apparatus is a magnetoresistive sensor that senses said external magnetic field component.

27. An apparatus as recited in claim 25 wherein said receiver apparatus includes a display of said sensed external magnetic field.

28. The apparatus of claim 16 wherein said transducer produces a rotational movement in response to a failure of said corrosion coupon.

29. The apparatus of claim 16 wherein said transducer produces a translational movement in response to a failure of said corrosion coupon.

* * * * *